US012673110B2

(12) United States Patent
Fang

(10) Patent No.: US 12,673,110 B2
(45) Date of Patent: Jul. 7, 2026

(54) USE OF ANTI-HER2 ANTIBODY-DRUG CONJUGATE IN TREATING UROTHELIAL CARCINOMA

(71) Applicant: RemeGen Co., Ltd., Yantai (CN)

(72) Inventor: Jianmin Fang, Yantai (CN)

(73) Assignee: RemeGen Co., Ltd., Yantai (CN)

( * ) Notice: Subject to any disclaimer, the term of this patent is extended or adjusted under 35 U.S.C. 154(b) by 279 days.

(21) Appl. No.: 16/652,413

(22) PCT Filed: Aug. 19, 2019

(86) PCT No.: PCT/CN2019/101283
§ 371 (c)(1),
(2) Date: Mar. 30, 2020

(87) PCT Pub. No.: WO2020/042941
PCT Pub. Date: Mar. 5, 2020

(65) Prior Publication Data
US 2020/0289663 A1     Sep. 17, 2020

(30) Foreign Application Priority Data

Aug. 29, 2018    (CN) .......................... 201810998055.4

(51) Int. Cl.
*A61K 47/68*        (2017.01)
*A61K 9/00*         (2006.01)
(Continued)

(52) U.S. Cl.
CPC .... *A61K 47/68031* (2023.08); *A61K 47/6817* (2017.08); *A61K 47/6861* (2017.08);
(Continued)

(58) Field of Classification Search
CPC ............ A61K 47/6817; A61K 47/6803; A61K 47/6861; A61K 47/6847; A61K 47/6855;
(Continued)

(56) References Cited

U.S. PATENT DOCUMENTS

| | | | |
|---|---|---|---|
| 5,635,483 A | 6/1997 | Pettit | |
| 8,241,639 B2 | 8/2012 | Middeldorp | |

(Continued)

FOREIGN PATENT DOCUMENTS

| | | | |
|---|---|---|---|
| AU | 2014352475 A1 | 2/2016 | |
| AU | 2020239621 A1 | 10/2020 | |

(Continued)

OTHER PUBLICATIONS

Vlachostergios, P.J., et al (2018) Antibody-Drug Conjugates in Bladder Cancer Bladder Cancer 4; 247-259 (published Jul. 30, 2018) (Year: 2008).*

(Continued)

*Primary Examiner* — Scarlett Y Goon
*Assistant Examiner* — Audrey L Buttice
(74) *Attorney, Agent, or Firm* — McNeill PLLC

(57)           ABSTRACT
The present invention relates to the use of an anti-HER2 antibody-drug conjugate (ADC) in preparing a drug for treating urothelial carcinoma. The drug is safe and effective for patients with urothelial carcinoma, especially locally advanced or metastatic urothelial carcinoma, and can effectively prolong the survival time of the patients.

17 Claims, 9 Drawing Sheets

Specification includes a Sequence Listing.

(51) Int. Cl.

| | | |
|---|---|---|
| *A61K 9/19* | (2006.01) | |
| *A61K 45/06* | (2006.01) | |
| *A61P 35/00* | (2006.01) | |
| *C07K 16/32* | (2006.01) | |

(52) U.S. Cl.
CPC ............. *A61P 35/00* (2018.01); *C07K 16/32* (2013.01); *A61K 9/0021* (2013.01); *A61K 9/0043* (2013.01); *A61K 9/19* (2013.01); *A61K 45/06* (2013.01); *C07K 2317/24* (2013.01); *C07K 2317/565* (2013.01)

(58) Field of Classification Search
CPC ...... A61K 9/0021; A61K 9/0043; A61K 9/19; A61K 45/06; A61K 38/00; A61K 38/05; A61K 31/5365; A61P 35/00; A61P 13/02; C07K 16/32; C07K 2317/24; C07K 2317/565; C07K 2317/77; C07K 2317/92
See application file for complete search history.

(56) References Cited

U.S. PATENT DOCUMENTS

| | | | |
|---|---|---|---|
| 9,345,785 | B2 | 5/2016 | Law |
| 9,457,093 | B2 | 10/2016 | Fry et al. |
| 10,087,260 | B2 | 10/2018 | Fang et al. |
| 2005/0009751 | A1 | 1/2005 | Senter et al. |
| 2005/0053666 | A1 | 3/2005 | Tzannis et al. |
| 2008/0311134 | A1 | 12/2008 | Junutula |
| 2011/0177095 | A1 | 7/2011 | Harding et al. |
| 2011/0177099 | A1 | 7/2011 | Lackner et al. |
| 2011/0217305 | A1 | 9/2011 | Pedersen et al. |
| 2011/0256135 | A1 | 10/2011 | Fraunhofer et al. |
| 2012/0027270 | A1 | 2/2012 | Kyyko et al. |
| 2012/0039942 | A1 | 2/2012 | Bos et al. |
| 2013/0060010 | A1 | 3/2013 | Williams et al. |
| 2013/0171148 | A1 | 7/2013 | De et al. |
| 2013/0189271 | A1 | 7/2013 | De Goeij et al. |
| 2013/0243762 | A1 | 9/2013 | Vafa et al. |
| 2014/0286969 | A1 | 9/2014 | Tschoepe et al. |
| 2015/0080559 | A1 | 3/2015 | Miao et al. |
| 2016/0304621 | A1 | 10/2016 | Fang et al. |
| 2016/0333112 | A1 | 11/2016 | Naito et al. |
| 2017/0209594 | A1 | 7/2017 | Goldenberg et al. |
| 2018/0110772 | A1 | 4/2018 | Govindan et al. |
| 2018/0200382 | A1 | 7/2018 | Osinga et al. |
| 2018/0243435 | A1 | 8/2018 | Dylla et al. |
| 2018/0271996 | A1 | 9/2018 | Bodyak et al. |
| 2019/0030180 | A1 | 1/2019 | Harlow et al. |
| 2019/0091345 | A1 | 3/2019 | Miao et al. |
| 2019/0330196 | A1 | 10/2019 | Chen et al. |
| 2019/0330368 | A1 | 10/2019 | Jikoh et al. |
| 2020/0289663 | A1 | 9/2020 | Fang |
| 2021/0093730 | A1 | 4/2021 | Sperber et al. |
| 2021/0101888 | A1 | 4/2021 | Pazolli et al. |
| 2021/0101982 | A1 | 4/2021 | Kwan et al. |
| 2021/0128741 | A1 | 5/2021 | Kamii et al. |
| 2021/0154314 | A1 | 5/2021 | Li et al. |
| 2021/0238305 | A1 | 8/2021 | Yu et al. |
| 2021/0252006 | A1 | 8/2021 | Xue et al. |
| 2021/0393794 | A1 | 12/2021 | Zhu et al. |
| 2022/0143009 | A1 | 5/2022 | Iwata et al. |
| 2022/0177590 | A1 | 6/2022 | Fang et al. |
| 2022/0281972 | A1 | 9/2022 | Liu et al. |
| 2022/0283167 | A1 | 9/2022 | Nishikawa et al. |
| 2022/0387618 | A1 | 12/2022 | Walker et al. |
| 2024/0025947 | A1 | 1/2024 | Li et al. |
| 2024/0033368 | A1 | 2/2024 | Li et al. |
| 2024/0148894 | A1 | 5/2024 | Fang et al. |
| 2024/0207424 | A1 | 6/2024 | Fang et al. |
| 2024/0207431 | A1 | 6/2024 | Fang et al. |

FOREIGN PATENT DOCUMENTS

| | | | |
|---|---|---|---|
| CA | 2376596 | A1 | 1/2001 |
| CA | 2872226 | A1 | 11/2013 |
| CA | 2919359 | A1 | 5/2015 |
| CA | 3085001 | A1 | 10/2020 |
| CA | 3073388 | A1 | 8/2021 |
| CN | 1938046 | A | 3/2007 |
| CN | 101143902 | A | 3/2008 |
| CN | 101143902 | B1 | 3/2008 |
| CN | 101687037 | A | 3/2010 |
| CN | 102027135 | A | 4/2011 |
| CN | 102027135 | B2 | 4/2011 |
| CN | 102030827 | A | 4/2011 |
| CN | 102167742 | A | 8/2011 |
| CN | 102884084 | A | 1/2013 |
| CN | 102892430 | A | 1/2013 |
| CN | 103153339 | A | 6/2013 |
| CN | 103154035 | A | 6/2013 |
| CN | 103319599 | A | 9/2013 |
| CN | 105008398 | A | 10/2015 |
| CN | 105163763 | A | 12/2015 |
| CN | 105267982 | A | 1/2016 |
| CN | 105968038 | A | 9/2016 |
| CN | 106999605 | A | 8/2017 |
| CN | 107029244 | A | 8/2017 |
| CN | 107789631 | A | 3/2018 |
| CN | 107847449 | A | 3/2018 |
| CN | 108473591 | A | 8/2018 |
| CN | 108743968 | A | 11/2018 |
| CN | 109200291 | A | 1/2019 |
| CN | 109320612 | A | 2/2019 |
| CN | 110049779 | A | 7/2019 |
| CN | 111670201 | A | 9/2020 |
| CN | 112353947 | A | 2/2021 |
| CN | 112402616 | A | 2/2021 |
| CN | 113603842 | A | 11/2021 |
| EP | 1210372 | | 6/2002 |
| EP | 3072907 | A1 | 9/2016 |
| EP | 3480215 | A1 | 5/2019 |
| JP | H1033474 | A | 2/1998 |
| JP | 2010523469 | A | 7/2010 |
| JP | 2012500180 | A | 1/2012 |
| JP | 2013529904 | A | 7/2013 |
| JP | 2013534809 | A | 9/2013 |
| JP | 2016528902 | A | 9/2016 |
| JP | 2017529345 | A | 10/2017 |
| JP | 2019502650 | A | 1/2019 |
| KR | 20140037105 | A | 3/2014 |
| KR | 101854443 | B1 | 6/2018 |
| KR | 101993136 | B1 | 6/2019 |
| KR | 102520974 | B1 | 4/2023 |
| RU | 2270029 | A | 2/2006 |
| RU | 2270029 | C2 | 2/2006 |
| RU | 2006147264 | A | 7/2008 |
| RU | 2683780 | C2 | 4/2019 |
| TW | I767139 | B | 6/2022 |
| WO | 200109187 | A2 | 2/2001 |
| WO | 200109187 | A3 | 8/2001 |
| WO | 200187336 | A1 | 11/2001 |
| WO | 2004060343 | A1 | 7/2004 |
| WO | 2005081711 | A2 | 9/2005 |
| WO | 2005117986 | A2 | 12/2005 |
| WO | 2005117986 | A3 | 6/2006 |
| WO | 2005081711 | A3 | 11/2006 |
| WO | 2008150485 | A2 | 12/2008 |
| WO | 2008150485 | A3 | 4/2009 |
| WO | 2009117277 | A2 | 9/2009 |
| WO | 2009117277 | A3 | 4/2010 |
| WO | 2011107957 | A1 | 9/2011 |
| WO | 2011147982 | A2 | 12/2011 |
| WO | 2011147982 | A3 | 3/2012 |
| WO | 2012143523 | A1 | 10/2012 |
| WO | 2012166559 | A1 | 12/2012 |
| WO | 2014143765 | A1 | 9/2014 |
| WO | 2015057699 | A2 | 4/2015 |
| WO | 2015074528 | A1 | 5/2015 |
| WO | 2015177360 | A1 | 11/2015 |
| WO | 2016044396 | A1 | 3/2016 |

(56) References Cited

FOREIGN PATENT DOCUMENTS

| WO | 2016046574 A1 | 3/2016 |
|---|---|---|
| WO | 2016064649 A1 | 4/2016 |
| WO | 2016180941 A1 | 11/2016 |
| WO | 2016196298 A1 | 12/2016 |
| WO | 2017009255 A1 | 1/2017 |
| WO | 2018102589 A2 | 6/2018 |
| WO | 2018233572 A1 | 12/2018 |
| WO | 2019027520 A1 | 2/2019 |
| WO | 2019034177 A1 | 2/2019 |
| WO | 2019039483 A1 | 2/2019 |
| WO | 2019081807 A1 | 5/2019 |
| WO | 2019223653 A1 | 11/2019 |
| WO | 2020042941 A1 | 3/2020 |
| WO | 2020192693 A1 | 10/2020 |
| WO | 2021086981 A1 | 5/2021 |
| WO | 2021097220 A1 | 5/2021 |
| WO | 2022034504 A1 | 2/2022 |
| WO | 2022058871 A1 | 3/2022 |
| WO | 2022067347 A1 | 3/2022 |
| WO | 2022098972 A1 | 5/2022 |
| WO | 2022174775 A1 | 8/2022 |
| WO | 2022206870 A1 | 10/2022 |
| WO | 2022206871 A1 | 10/2022 |
| WO | 2022212899 A1 | 10/2022 |
| WO | 2022242692 A1 | 11/2022 |
| WO | 2022247708 A1 | 12/2022 |
| WO | 2023114871 A1 | 6/2023 |
| WO | 2023143343 A1 | 8/2023 |

OTHER PUBLICATIONS

Burris, H.A., et al (2011) Trastuzumab Emtansine (T-DM1): A Novel Agent for Targeting HER2+ Breast Cancer Clinical Breast Cancer 11(5); 275-282 (Year: 2011).*

Agarwal, P., and C.R. Bertozzi (2014) Site-specific antibody-drug conjugates: the nexus of biorthogonal chemistry, protein engineering, and drug development Bioconjugate Chemistry 26; 176-192 (Year: 2014).*

The Clinical Pharmacology and Biopharmaceutics Review of Kadcyla (Trastuzumab emtansine (T-DM1) by the Center for Drug Evaluation and Research, Sep. 19, 2012 (Year: 2012).*

Li, Y., et al (2014) Characterization and Stability Study of Polysorbate 20 in Therapeutic Monoclonal Antibody Formulation by Multidimensional Ultrahigh-Performance Liquid Chromatograph-Charged Aerosol Detection—Mass Spectrometry Analytical Chemistry 86; 5150-5157 (Year: 2014).*

Chen, H., et al (2017) Tubulin Inhibitor-Based Antibody-Drug Conjugates for Cancer Therapy Molecules 22(1281); 1-28 (Year: 2017).*

Hansel, D.E., et al (2008) HER2 Overexpression and Amplification in Urothelial Carcinoma of the Bladder is Associated with MYC Coamplification in a Subset of Cases Am J Clin Pathol 130; 274-281 (Year: 2008).*

Li, H., et al (2016) An anti-HER2 antibody conjugated with monomethyl auristatin E is highly effective in Her2-positive human gastric cancer Cancer Biology & Therapy 17(4); 346-354 (Year: 2016).*

Parslow, A., et al (2016) Antibody-Drug Conjugates for Cancer Therapy Biomedicines 4(14); 1-17 (Year: 2016).*

Rabia, L.A et al (2018) Understanding and overcoming trade-offs between antibody affinity, specificity, stability and solubility Biochem Eng J 137; 365-374 (Year: 2018).*

Barok, M., et al (2014) Trastuzumab emtansine: mechanisims of action and drug resistance Breast Cancer Research 16(209) 1-12. (Year: 2014).*

Levengood, M.R., et al (2017) Orthogonal Cysteine Protection Enables Homogeneous Mult-drug Antibody-Drug Conjugates Angew Chem Int Ed 56; 733-737 (Year: 2017).*

A.I. Shcherbakov et al., "Affinity Properties of Plant-Made ANTI-HER2 Antibodies", Russina Journal of Biotherapy, 2018, vol. 17, No. 1, pp. 95-100; total 7 pages.

Nepomnyashchikh T.S., et al., "Short Overview of Clinical Trials With Current Immunotherapeutic Tools for Cancer Treatment", Medical Immunology(Russia), 2017, vol. 19, No. 2, pp. 127-144; total 19 pages.

International Search Report mailed on Nov. 18, 2019 in the corresponding International application(application No. PCT/CN2019/101283).

Panagiotis J. Vlachostergiosa et al., "Antibody-Drug Conjugates in Bladder Cancer", 13 pages.

"Chinese Original Research and Development of ADC Drugs appeared on the international stage, bringing a breakthrough in the treatment of HER2 positive uepithelial carcinoma", Jun. 5, 2019, 10 pages.

Mei-ren Li et al., "Gene Amplification and Protein Expression of the Human Epidermal Growth Factor Receptor 2 in Urothelial Carcinoma of Bladder", in Aug. 2015, 5 pages.

ATCC, CRL-1580 (Apr. 11, 2019). "P3X63Ag8.653, Mouse Cell Line STR Profile from ATCC," 3 pages.

Azyolinsky, A et al. (Jun. 5, 2014). 2014 NCCN Guidelines Updated: Experts Highlight New Recommendations for Clinical Practice, 7 pages.

Bellmunt, J. et al. (2009). "Phase III Trial of Vinflunine Plus Best Supportive Care Compared With Best Supportive Care Alone After a Platinum-Containing Regimen in Patients With Advanced Transitional Cell Carcinoma of the Urothelial Tract," J Clin. Oncol. 27 (27):4454-4461.

Burke, P.J. et al. (Aug. 2018). "Glucuronide-Linked Antibody-Tubulysin Conjugates is Play Activity in MDR+ and Heterogeneous Tumor Models," Molecular Cancer Therapeutics 17(8):1752-1760.

Chung, Y.-C. et al. (2018, e-pub. Mar. 2, 2018). "Metformin-Induced Caveolin-1 Expression Promotes T-DM1 Drug Efficacy in Breast Cancer Cells," Scientific Reports 8:3930, 9 pages.

Cui, Y. et al. (2017, e-pub. Jan. 4, 2017). "Monoclonal Antibodies: Formulations of Marketed Products and recent Advances in Novel Delivery System," Drug Development and Industrial Pharmacy 43(4):519-530.

Daugherty, A.L. et al. (2010). "Formulation and Delivery Issues for Monoclonal Antibody Therapeutics," Chapter 8 in Current Trends in Monoclonal Antibody Development and Manufacturing, Biotechnology: Pharmaceutical Aspects, S.J. Shrine (ed.) et al., Springer, pp. 103-129.

Extended European Search Report, dated Feb. 2, 2022, for European Patent Application No. 20776430.09, 8 pages. .

Extended European Search Report, dated May 13, 2022, for European Patent Application No. 19855043.6, 9 pages. .

Extended European Search Report, dated May 16, 2017, for European Patent Application No. 14864053.5, 8 pages.

International Preliminary Report on Patentability, issued Mar. 2, 2021, for PCT Application No. PCT/CN2019/101283, filed Aug. 19, 2019, 5 pages. .

International Preliminary Report on Patentability, issued May 24, 2016, for PCT Application No. PCT/CN2014/091332, filed Nov. 18, 2014, 5 pages. .

International Preliminary Report on Patentability, issued Sep. 28, 2021, for PCT Application No. PCT/CN2020/081138, filed Mar. 25, 2020, 6 pages.

International Search Report and Written Opinion, Jul. 3, 2020, for PCT Application No. PCT/CN2020/081138, filed Mar. 25, 2020, 24 pages. .

International Search Report, and Written Opinion mailed Feb. 11, 2015, for PCT Application No. PCT/CN2014/091332, filed Nov. 18, 2014, English Translation, 17 pages. .

Iqbal, N. et al. (Sep. 7, 2014). "Human Epidermal Growth Factor Receptor 2 (HER2) in Cancers: Overexpression and Therapeutic Implications," Molecular Biology International 2014(852748):1-10.

Miao, Q.-F. et al. (2012). "An Overview of Antibody-Based Cancer Therapy," Acta Pharmaceutica Sinica 47(10):1261-1268. English Abstract, 8 pages.

NCT02365597 (Nov. 14, 2022). "An Efficacy and Safety Study of Erdafitinib (JNJ-42756493) in Participants With Urothelial Cancer," 9 pages.

(56)                References Cited

OTHER PUBLICATIONS

Orosz, F. et al. (Dec. 15, 2002). "A Simple Method for the Determination of Dissociation Constants by Displacement ELISA," Journal of Immunological Methods, 270(2):155-162.

Rockberg, J. et al. (2009, e-pub. Jan. 31, 2009). "Discovery of Epitopes for Targeting the Human Epidermal Growth Factor Receptors 2 (HER2) with Antibodies," Molecular Oncology 3:238-247.

Singh, R. et al. (Jun. 2016, e-pub. Mar. 29, 2016). "A New Triglycyl Peptide Linker for Antibody-Drug Conjugates (ADCs) with Improved Targeted Killing of Cancer Cells," MCT 15(6):1311-1320.

Von Minchwitz, G. et al. (Jun. 1, 2005). "Phase I Clinical Study of the Recombinant Antibody Toxin scFv(FRP5)—ETA Specific for the ErbB2/HER2 Receptor in Patients with Advanced Solid Malignomas," Breast Cancer Research 7: R617-R626.

Wakankar, A.A. et al. (Nov. 2006). "Formulation considerations for Proteins Susceptible to Asparagine Deamidation and Aspartate Isomerization," J. Pharm. Sci. 95(11):2321-2336.

WHO Technical Report Series, No. 822, 1992 Annex 3, 92 pages.

Yafi, F.A. et al. (2011). "First-and Second-Line Therapy for Metastatic Urothelial Carcinoma of the Bladder," Current Oncol. 18 (1):e25-e34.

Yu, S. et al. (2017). "Development and Clinical Application of Anti-HER2 Monoclonal and Bispecific Antibodies for Cancer Treatment," Experimental Hematology Oncology 6:31, 15 pages.

Zhang, M. et al. (2003). "The New Progress of the Study for Anti-Her2 Monoclonal Antibody," Foreign Medical Sciences, Section of Pathophysiology and Clinical Medicine 23(3):257-259. English Abstract, 4 pages.

Zhu, G.-D. et al. (2013). "Design of Next Generation Antibody Drug Conjugates," Acta Pharmaceutica Sinica 48(7):1053-1070. English Abstract, 18 pages.

Zhou, I. et al. (2016). "Research Progress of Maytansinoid Antibody Drug Conjugates," Chinese Journal of New Drugs 25(22):2521-2530, English Abstract, 10 pages.

Clinicaltrials.gov (Apr. 24, 2018). "NCT03507166—A Phase II Study of RC48-ADC in Subjects with HER2 Positive Metastatic or Unresectable Urothelial Cancer," 7 pages.

Davies, J. et al. (1996) "Affinity Improvement of Single Antibody VH Domains: Residues In All Three Hypervariable Regions Affect Antigen Binding," Immunol. 2:169-179.

Holt, L.J. et al. (Nov. 2003). "Domain Antibodies: Proteins for Therapy," Trends in Biotechnology 21(11):484-490.

Jiang, J. et al. (2016, e-pub. Aug. 7, 2016). "HER2-Targeted Antibody Drug Conjugates for Ovarian Cancer Therapy," European Journal of Pharmaceuticals Sciences 93:274-286.

Jiang, J. et al. (2020). "Preclinical Safety Profile of Disitamab Vedotin: A Novel Anti-HER2 Antibody Conjugated with MMAE," Toxicology Letters 324:30-37.

Peng, Z. et al. (2020, e-pub. May 25. 2020). "Abstract: 4560—A Phase II Study of Efficacy and Safety of RC48-ADC in Patients with Locally Advanced or Metastatic HER2-Overexpressing Gastric or Gastroesophageal Junction Cancers," Journal of Clinical Oncology, 1 page.

Phillips, G.D.L. et al. (Nov. 15, 2008). "Targeting HER2-Positive Breast Cancer with Trastuzumab-DM1, an Antibody-Cytotoxic Drug Conjugate," Cancer Res 68:(22):9280-9290.

Sheng, X. et al. Oct. 27, 2020). "Open-Label, Multicenter, Phase II Study of RC48-ADC, A HER2-Targeting Antibody-Drug Conjugate, in Patients with Locally Advanced or Metastatic Urothelial Carcinoma," Clinical Cancer Research 27(1):43-51.

Wang, J. et al. (May 20, 2021). "RC48-ADC, A HER2-Targeting Antibody-Drug Conjugate, in Patients with HER2-Positive and HER2-Low Expressing Advanced or Metastatic Breast Cancer: A Pooled Analysis of Two Studies," Journal of Clinical Oncology 39(15 Suppl)1022, Abstract: 1022. 4 pages.

Xu, B. et al. (2018, e-pub. Jun. 1, 2018). "Abstract: 1028—An Open-Label, Multicenter, Phase IB Study to Evaluate RC48-ADC in Patients with HER2-Positive Metastatic Breast Cancer," Journal of clinical Oncology, 1 page.

Yao, X. et al. (2015, e-pub. Aug. 8, 2015). "A Novel Humanized Anti-Her2 Antibody Conjugated with MMAE Exerts Potent Anti-Tumor Activity," Breast Cancer Treat. 153:123-133.

Zhou, L. et al. (May 20, 2021). "RC48-ADC Combined with Toripalimab, an Anti-PD-1 Monoclonal Antibody (Ab), in Patients with Locally Advanced or Metastatic Urothelial Carcinoma (UC): Preliminary Results of a Phase Ib/II Study," Journal of Clinical Oncology 39(15 supl):4534, Abstract 4534, 4 pages.

Anonymous (Jun. 3, 2018). "Abstract # 4503-Erdafitinib Phase 2 Study Results Show Promise in the Treatment of Metastatic Urothelial Cancer," retrieved from the Internet: <https:www.jnj.com/media-center/press-relases/eradfitinib-phase-2-study-results-show-promise-in-the-treatment-of-metastatic-urothelial-cancer>, last visited Apr. 25, 2023, 3 pages.

Anonymous (Aug. 7, 2023). "A Study of RC48-ADC Combination Therapies as First-Line Treatment in Advanced Metastatic Gastric Cancer," ICH GCP, US Clinical Trials Registry, 21 pages.

Anonymous (Oct. 17, 2020). "Global Burden of 369 Diseass and Injuries in 204 Conutries and Territories, 1990-2019: A Systematic Analysis for the Global Burden of Diseas Study 2019," Lancet 396(10258):1204-1222, 40 pages.

Arbyn, M. et al. (Feb. 2020). "Estimates of Incidence and Mortality of Cervical Cancer in 2018: A WorldWide Analysis," Lancet Glob. Health 8:e191-e203.

Bachelot, T. et al. (2019, e-pub. Feb. 23, 2019). "Preliminary Safety and Efficacy of First-Line Pertuzumab Combined with Trastuzumab and Taxane Therapy for HER2-Postive Locally Recurrent or Metastatic Breast Cancer (PERUSE)," Ann. Oncol. 30(5):766-773.

Baselga, J. et al. (Jan. 12, 2012). "Pertuzumab Plus Trastuzumab Plus Docetaxel for Metastatic Breast Cancer," N. Engl. J. Med. 366(2):109-119.

Beck, A. et al. (May 2017; e-pub. Mar. 17, 2017). "Strategies and Challenges for the Next Generation of Antibody-Drug Conjugates," Nature Rev Drug Discovery 16(5):315-337.

Cardoso, F. et al. (2018, e-pub. Jul. 19, 2018). "4th ESO-ESMO International Consensus Guidelines for Advanced Breast Cancer (ABC4)+," Ann. Oncol. 29(8):1634-1657.

Cardoso, F. et al. (2019, e-pub. Jun. 4, 2019). "Early Breast Cancer: ESMO Clincal Practice Guidelines for Diagnosis, Treatment and Follow-Up," Ann. Oncol. 30(8):1194-1220.(Dec. 1, 2023).

CAS Registry No. 1859072-53-9 (Feb. 5, 2019). "PDR 001," 6 pages.

Cibula, D. et al. (2018). "The European Society of Gynaecological Oncology/European Society for Radiotherapy and Oncology/European Society of Pathology Guidelines for the Management of Patients With Cervical Cancer," Int. J. Gynecol. Cancer 28:641-655.

Clinicaltrials (Jul. 30, 2021). "CTR20211602—Recombinant Humanized Anti-HER2 Monoclonal Anti-MMAE Conjugator for Injection Former Name," 14 pages with English Translation.

Clinicaltrials.gov (Apr. 6, 2017). "NCT03113266—A Study and Efficacy of Toripalimab for Patients with Locally Advanced or Metastatic Bladder Urothelial Carcinoma," 12 pages.

Clinicaltrials.gov (Aug. 26, 2016). "NCT02881138—A Study of RC48-ADC in Subjects with HER2-Positive Advanced Malignant Solid Tumors," 7 pages.

Clinicaltrials.gov (Feb. 14, 2017). "NCT03052634—A Study of RC48-ADC in Subjects with Advance Breast Cancer," 8 pages.

Clinicaltrials.gov (Feb. 21, 2020). "NCT04280341—JS001 | Combination with RC48-ADC in Treatment of HER2-Postive Advance Malignant Solid Tumors," 8 pages.

Clinicaltrials.gov (Jul. 16, 2021). "NCT04965519—A Study of RC48-ADC for the Treatment of HER2-Expressing Gynecological Malignancies," 8 pages.

Colombo, P.E. et al. (2013). "Endometrial Cancer: ESMO Clinical Practice Guidelines for Diagnosis, Treatment and Follow-Up," Ann. Oncol. 24(Suppl 6):vi33-vi38.

Cortés, J. et al. (Mar. 24, 2022). "Trastuzumab Deruxtecan Versus Trastuzumab Emtansine for Breast Cancer," N. Engl. J. Med. 386(12):1143-1154.

Cronin, K.A. et al. (Nov. 2010). "Population-Based Estimate of the Prevalence of HER-2 Positive Breast Cancer Tumors for Early Stage Patients in the US," Cancer Invest. 28(9):963-968, 13 pages.

(56) References Cited

OTHER PUBLICATIONS

Cutsem, E.V. et al. (2019). "Binimetinib, Encorafenib, and Cetuximab Triplet Therapy for Patients with Braf V600E—Mutant Metastic Colorectal Cancer: Safety Lead-In Results from the Phase III Beacon Colorectal Cancer Study," J. Clin. Oncol. 37:1460-1469.

Deng, T. et al. (May 18, 2023). "Efficacy and Survival of Anti-PD-1 Antibody in Combination with Trastuzumab and Chemptherapy Versus Trastuzumab and Chemotherapy as First-Line Treatment of Her2-Positive Metastasis Gastric Adenocarcinoma: A Retrospective Study," Front Oncol. 13:1166040, 10 pages.

Du Bois, A. et al. (Sep. 3, 2003). A Randomized Clinical Trial of Cisplatin/Paclitaxel Versus Carboplatin/Paclitaxel as First-Line Treatment of Ovarian Cancer J. Natl. Cancer Inst. 95(17):1320-1329.

Dürr, C.V. (Jul. 4, 2018). Studies on the Physicochemical Stability of Antibody Conjugates, 127 pages.

Eiger, D. et al. (Mar. 1, 2021). "The Exciting New Field of HER2-Low Breast Cancer Treatment," Cancers (Basel) 13(5):1015, 18 pages.

Eisenhauser, E.A. et al. (Jan. 2009). "New Response Evaluation Criteria in Solid Tumours: Revised RECIST Guideline (version 1.1)," Eur. J. Cancer 45(2):228-247.

GenBank Accession No. NM_004448, last updated Feb. 12, 2023, located at https://www.ncbi.nlm.nih.gov/nuccore/NM_004448, last visited on Mar. 6, 2023, 9 pages.

GenBank Reference No. NP_001005862 (Oct. 2, 2023). "Receptor Tyrosine-Protein Kinase erbB-2 Isoform b [Homo sapiens]," 3 pages.

GenBank Reference Nos. NP 001276865 (Aug. 4, 2021). "Receptor Tyrosine-Protein Kinase erbB-2 isoform c [Homo sapiens],", 4 pages.

GenBank Reference Nos. NP 001276866 (Aug. 4, 2021). "Receptor Tyrosine-Protein Kinase erbB-2 isoform d precursor [Homo sapiens],", 5 pages.

GenBank Reference Nos. NP 001276867 (Aug. 4, 2021). "Receptor Tyrosine-Protein Kinase erbB-2 isoform e [Homo sapiens],", 3 pages.

GenBank Reference Nos. NP 001289936 (Feb. 16, 2021). "N(G),N(G)-dimethylarginine dimethylaminohydrolase 2 [Homo sapiens],", 3 pages.

GenBank Reference Nos. NP 001289937 (Dec. 12, 2020). "N(G),N(G)-dimethylarginine dimethylaminohydrolase 2 [Homo sapiens],", 3 pages.

GenBank Reference Nos. NP 001289938 (Apr. 26, 2021). "Arogenate Dehydrogenase 1, Chloroplastic-Like [Glycine max],", 2 pages.

GenBank Reference Nos. NP 004439 (Aug. 4, 2021). "Receptor Tyrosine-Protein Kinase erbB-2 Isoform a Precursor [Homo sapiens],", 6 pages.

Gennigens, C. et al. (2022, e-pub. Sep. 13, 2022). "Recurrent or Primary Metastatic Cervical Cancer: Current and Future Treatments," ESMO Open 7(5):100579, 14 pages.

Geyer, C.E. et al. (Dec. 28, 2006). "Lapatinib Plus Capecitabine for HER2-Positive Advanced Breast Cancer," N. Engl. J. Med. 355(26):2733-2743.

Giordano, S.H. et al. (Jul. 1, 2014). "Systemic Therapy for Patients with Advanced Human Epidermal Growth Factor Receptor 2-Positive Breast Cancer: American Society of Clinical Oncology Clinical Practice Guideline," J. Clin. Oncol. 32(19):2078-2099.

Guo, L. et al. (Jan. 30, 2020). "Global Approved New Drugs in 2019: Reported and Prospect," Journal of Multidisciplinary Cancer Management 6(1):70-79. English Abstract Translation.

Hanna, N.H. et al. (Jan. 28, 2020, e-pub. Oct. 6, 2023). "Therapy for Stage IV Non-Small-Cell Lung Cancer Without Driver Alterations: ASCO and OH (CCO) Joint Guideline Update," J. Clin. Oncol. 38(14):1608-1632.

Hellmann, M.D. et al. (Nov. 21, 2019). "Nivolumab Plus Ipilimumab in Advanced Non-Small-Cell Lung Cancer," N. Engl. J. Med. 381(21):2020-2031.

Hsu, A. et al. (2020). "Treatment for Metastatic Adenocarcinoma of the Stomach and Gastroesophageal Junction: 2020," Ann. Transl. Med. 8(17):1109, 11 pages.

Hu, X. et al. (Dec. 2017). "Research Progress of Bullet Molecules of Antibody-Drug Conjugates," Chin Med Biotechnol, 12(6):549-555. English Translation of Introduction and Conclusion, 9 pages.

Huang, L. et al. (Oct. 16, 2021). "A HER2-Target Antibody Drug Conjugate Combined with Anti-PD-(L)1 Treatment Eliminates hHER2 + Tumores in hPD-1 Transgenic Mouse Model and Contributes Immune Memory Formation," Breast Cancer Research and Treatment 191(1):51-61, 16 pages.

International Preliminary Report on Patentability, issued Aug. 22, 2023, for PCT Application No. PCT/CN2022/076554, filed Feb. 17, 2022, 4 pages. (Dec. 1, 2023).

International Preliminary Report on Patentability, issued Oct. 3, 2023, for PCT Application No. PCT/CN2022/084236, filed Mar. 31, 2022, 6 pages.

International Preliminary Report on Patentability, issued Oct. 3, 2023,for PCT Application No. PCT/CN2022/084238, filed Mar. 31, 2022, 5 pages.

International Search Report, and Written Opinion mailed Aug. 16, 2022, for PCT Application No. PCT/CN2022/093631, filed May 18, 2022, 14 pages.

International Search Report, and Written Opinion mailed Aug. 19, 2022, for PCT Application No. PCT/CN2022/093632, filed May 18, 2022, 12 pages.

International Search Report, and Written Opinion mailed Jun. 27, 2022, for PCT Application No. PCT/CN2022/084238, filed Mar. 31, 2022, 8 pages.

International Search Report, and Written Opinion mailed Jun. 28, 2022, for PCT Application No. PCT/CN2022/084236, filed Mar. 31, 2022, 10 pages.

International Search Report, and Written Opinion mailed May 12, 2022, for PCT Application No. PCT/CN2022/076554, filed Feb. 17, 2022, 9 pages.

Jackson, D. (Jan. 30, 2015). "Obama Pushes 'Precision Medicine Initiative'," USA Today, 2 pages.

Kulukian, A. et al. (Apr. 1, 2020). "Preclinical Activity of HER2-Selective Tyrosine Kinase Inhibitor Tucatinib as a Single Agent or in Combination with Trastuzumab or Docetaxel in Solid Tumor Models," Molecular Cancer Therapeutics 19(4):976-987.

Lattanzi, M. et al. (Jul. 31, 2020). "The Emergining Role of Antibody-Drug Conjugates in Urothelial Carcinoma," Expert Review of Anticancer Therapy 20(7):551-561, 24 pages.

Leeman, C.R. et al. (Jan. 2011, epub. Dec. 16, 2010.). "The Molecular Biology of Head and Neck Cancer," Nat. Rev. Cancer. 11(1):9-22.

Lengyel, C.G. et al. (Dec. 22, 2020). "Role of Her-2 in Gastrointestinal Tumours Beyond Gastric Cancer: A Tool for Precision Medicine," Gastrointert. Disord. 3(1):1-22.

León, X. et al. (Sep. 2005). "A Retrospective Analysis of the Outcome of Patients with Recurrent and/or Metastatic Squamous Cell Carcinoma of the Head and Neck Refractory to a Platinum-Based Chemotherapy," Clin. Oncol. (R. Coll. Radiol) 17(6):418-424.

Li, B. (Jun. 1-5, 2018). "Abstract 2502: A Multi-Histology Basket Trial of Adotrastuzumab Emtansine in Patients With HER2 Amplified Cancers," 2018 ASCO Annual Meeting, 3 pages.

Li, B. (Jun. 2, 2018). "Interview: A Multi-Histology Basket Trial of Adotrastuzumab Emtansine in Patients With HER2 Amplified Cancers," 2018 ASCO Annual Meeting, 10 pages.

Lin, N.U. et al. (May 29, 2020). "Intracranial Efficacy and Survival With Tucatinib Plus Trastuzumab and Capecitabine for Previously Treated HER2-Positive Breast Cancer With Brain Metastases in the HER2CLIMB Trial," J. Clin. Oncol. 38(23):2610-2619.

Menard, S. et al. (2003). "Biologic and Therapeutic Role of HER2 in Cancer," Oncogene 22(42):6570-6578.

Mendes, D. et al. (2015). "The Benefit of HER2-Targeted Therapies on Overall Survival of Patients with Metastatic HER2-Positive Breast Cancer—A Systematic Review," Breast Cancer Res. 17:140, 14pages.

Miles, D. et al. (2017, e-pub. Nov. 3, 2017). "Effect of Docetaxel Duration on Clinical Outcomes: Exploratory Analysis of CLEOPATRA, a Phase III Randomized Controlled Trial," Ann. Oncol. 28(11):2761-2767.

(56)　　References Cited

OTHER PUBLICATIONS

Moasser, M.M. et al. (Oct. 4, 2007). "The Oncogen HER2: Its Signaling and Transforming Functions and its Role in Human Cancer Pathogenesis," Oncogene 26:6469-6487, 32 pages.

Modi, S. et al. (Jul. 7, 2022). "Trastuzumab Deruxtecan in Previously Treated HER2-Low Advanced Breast Cancer," N. Engl. J. Med. 387(1):9-20.

Mountain, A. et al. (Dec. 1992, e-pub. Apr. 15, 2013). "Engineering Antibodies for Therapy," Biotechno. Genet. Eng. Rev. 10:1-143.

Murthy, R.K. et al. (Feb. 13, 2020). "Tucatinib, Trastuzumab, and Capecitabine for HER2-Positive Metastatic Breast Cancer," N. Engl. J. Med. 382(7):597-609.

NCT03500380 (Apr. 24, 2018). "A Study of RC48-ADC Administered Intravenously to Patients with HER2-Positive Metastatic Breast Cancer with or without Liver Metastases," 17 pages.

NCT04400695 (Sep. 29, 2020). "A Study of RC48-ADC for the Treatment of Locally Advanced or Metastatic Breast Cancer With Low Expression of HER2," 13 pages.

Neve, R.M. et al. (2001). "The Role of Overexpressed HER2 in Transformation," Ann. Oncol. 12(Supp. 11):S9-S13.

Nicolò, E. et al. (May 2022, e-pub. Apr. 18, 2022). "Combining Antibody-Drug Conjugates with Immunotherapy in Solid Tumors: Current Landscape and Future Perspectives," Cancer Treat. Rev. 106:102395, 12 pages.

Ozols, R.F. et al. (Sep. 1, 2003). "Phase III Trial of Carboplatin and Paclitaxel Compared with Cisplatin and Paclitaxel in Patients with Optimally Resected Stage III Ovarian Cancer: A Gynecolgic Onclolgy Group Study," J. Clin. Oncol. 21(17):3194-3200.

Powles, T. et al. (2016, e-pub. Oct. 31, 2016). "Phase III. Double-Blind, Randomized Trial That Compared Maintenance Laptinib Versus Placebo After First-Line Chemotherapy in Patients With Human Epidermal Growth Factor Receptor 1/2-Positive Metastatic Bladder Cancer," Journal of Clinical Oncology 35:48-55.

Press, M.F. et al. (Jul. 1990). "Expression of the HER-2/Neu Proto-Oncogene in Normal Human Adult and Fetal Tissues," Oncogene 5(7):953-962.

Riechmann, L. et al. (Mar. 24, 1988). "Reshaping Human Antibodies for Therapy," Nature 33(6162):323-327.

Rugo, H.S. et al. (2022). "Primary Results From TROPICS-O2: A Randomized Phase 3 Study of Sacituzumab Govitecan (SG) Versus Treatment of Physician's Choice (TPC) in Patients (Pts) with Hormone Receptor-Positive/HER2-Negative (HR+/HER2−) Advanced Breast Cancer," J. Clin. Oncol. 40:Abstract LBA1001, 1 page.

Schettini, F. et al. (2021). "Clinical, Pathological, and PAM50 Gene Expression Features of HER2-Low Breast Cancer," NPF Breast Cancer 7(1):1, 13 pages.

Singer et al., "Optimal Humanization of 1B4, an anti-CD18 Murine Monoclonal Antibody, is Achieved by Correct Choice of Human V-region Framework Sequences," J Immunol (1993) 150(7): 2844-2857.

Singla, H. et al. (2020). "HER2 Tyrosine Kinase Inhibitors in the Sensitization to Cancers Resistant to HER2 Antibodies," Crit. Rev. Oncol. 25(3):241-250.

Slamon, D.J. et al. (Mar. 15, 2001). "Use of Chemotherapy Plus a Monoclonal Antibody Against HER2 for Metastatic Breast Cancer That Overexpresses HER2," The New England Journal of Medicine 344(11):783-792.

Socinski, M.A. et al. (2018, e-pub. Nov. 23, 2017). "Current and Emergent Therapy Options for Advanced Squamous Cell Lung Cancer," J. Thorac. Oncol. 13(2):165-183.

Staudacher, A.R. et al. (2017, e-pub. Oct. 24, 2017). "Antibody Drug Conjugates and Bystanders Killing: Is Antigen-Dependent Internalisation Required?," Br. J. Cancer 117:1736-1742.

Stenger, M. (Sep. 17, 2018). "The ASCO Post, IMvigor211 Trial: Atezolizumab vs Chemotherapy in Platinum-Treated Advanced Urothelial Carcinoma," The ASCO Post, 4 pages.

Sung, et al. (May/Jun. 2020). "Global Cancer Statistics 2020: GLOBOCAN Estimates of Incidence and Mortality Worldwide for 36 Cancers in 185 Countries," CA: A Cancer Journal for Clinicians, 71, 209-249.

Tarantino, P. et al. (Apr. 24, 2020). "HER2-Low Breast Cancer : Pathological and Clinial Landscape," J. Clin. Oncol. 38(17):1951-1962.

U.S. Appl. No. 18/374,902, filed Sep. 29, 2023, Li et al. (Copy not submitted herewith pursuant to the waiver of 37 C.F.R. 1.98(a)(2)(iii) issued by the Office on Sep. 21, 2004).

U.S. Appl. No. 18/375,175, filed Sep. 29, 2023, Li et al. (Copy not submitted herewith pursuant to the waiver of 37 C.F.R. 1.98(a)(2)(iii) issued by the Office on Sep. 21, 2004).

U.S. Appl. No. 18/450,966, filed Aug. 16, 2023, Fang et al. (Copy not submitted herewith pursuant to the waiver of 37 C.F.R. 1.98(a)(2)(iii) issued by the Office on Sep. 21, 2004).

Uhler, M. et al. (Jan. 23, 2015). "Proteomics: Tissue-Based Map of the Human Proteome," Science 347 (6220):1260419, 11 pages.

UniProtKB/Swiss-Prot Accession No. Q15116 (No Date). "PDCD1_Human—Programmed Cell Death Protein 1," 11 pages.

Verhoeyan, M. et al. (Mar. 25, 1988). "Reshaping Human Antibodies: Grafting an Antilysozyme Activity," Science 239:1534-1536.

Verma, S. et al. (2012). "Trastuzumab Emtansine for HER2-Positive Advanced Breast Cancer," The New England Journal of Medicine 367(19):1783-1791.

Vermorken, J.B. et al. (Jun. 1, 2007). "Open-Label, Uncontrolled, Multicenter Phase II Study to Evaluate the Efficacy and Toxicity of Cetuximab as a Single Agent in Patients With Recurrent and/or Metastatic Squamous Cell Carcinoma of the Head and Neck Who Failed to Respond to Platinum-Based Therapy," J. Clin. Oncol. 25(16):2171-2177.

Warne, N.W. et al. (2011, e-pub. Mar. 13, 2011). "Development of High Concentraction Protein Biopharmaceuticals: The Use of Platform Approaches in Formulation Development," European Journal of Pharmaceutics and Biopharmaceutics 78:208-212.

Wolff, A.C. et al. (Jul. 10, 2018, e-pub. May 30, 2018). "Human Epidermal Growth Factor Receptor 2 Testing in Breast Cancer: American Society of Clinical Oncology/College of American Pathologists Clinical Practice Guideline Focused Update," J. Clin. Oncol. 36(20):2105-2122.

Wolff, A.C. et al. (Nov. 1, 2013, e-pub. Oct. 7, 2013). "Recommendations for Human Epidermal Growth Factor Receptor 2 Testing in Breast Cancer: American Society of Clinical Oncology/College of American Pathologist Clinical Practice Guideline Update," J. Clin. Oncology 31(31):3997-4013.

Xiao, Q.Q. et al. (Jan. 2021, e-pub. Dec. 22, 2020). "Retrospective Analysis of Prognostic Factors and Establishment of a Prognostic Model for Patients with HER2-Positive Advanced Breast Cancer," Journal of China Medical University 50(1):58-60. English Abstract.

Xiao, W.K. et al. (Dec. 31, 2018). "Risk Factors and Survival Outcomes in Patients with Breast Cancer and Lung Metastasis: A Population-Based Study," Cancer Medicine 7(3):922-930.

Xu, B.H. et al. (Feb. 15, 2020). "Early Clinical Development of RC48-ADC in Patients with HER2 Positive Meatstatic Breast Cancer," Cancer Res. 80(4 Supple.):Abstract PD4-06, 3 pages.

Xu, M. et al. (Nov. 1, 2022). "A Multicenter, Single-Arm, Phase II Trial of RC48-ADC Combined with Radiotherapy, PD-1/PD-L1 Inhibitor Sequential GM-CSF and IL-2 (PRaG3.0 Regimen) for the Treatment of HER2-Expressing Advance Solid Tumors," International Journal of Radiation Oncology*Biology*Physics 114(3):e428, 3 pages.

Xu, Y. et al. (2021, e-pub. May 4, 2021). "Phase I Study of the Recombinant Humanized Anti-HER2 Monoclonal Antibody-MMAE Conjugate RC48-ADC in Patients with HER2-Positive Advanced Solid Tumors," Gastric Cancer 24:913-925.

Zhang, C. et al. (2019). "Emerging Therapies for Non-Small Cell Lung Cancer," J. Hematol. Oncol. 12(1):45, 24 pages.

Anonymous (Jan. 28, 2010). "GSK's Tykerb® Receives Accelerated Approval for First-Line Combination Treatment of Hormone Receptor Positive, HER2+/ErbB2+ Metastatic Breast Cancer," Press Releases, 7 pages.

Arx, C.V. et al. (2023, e-pub. Dec. 24, 2022). "The Evolving Therapeutic Landscape of Trastuzumab-Drug Conjugates: Future Perspectives Beyond HER-2 Positive Breast Cancer," Cancer Treatment Reviews 113:102500, 13 pages.

(56)            References Cited

OTHER PUBLICATIONS

Bebbington, C.R. et al. (Feb. 1992). "High-Level Expression of a Recombinant Antibody from Myeloma Cells Using a Glutamine Synthetase Gene as an Amplifiable Selectable Marker," Bio Technology 10(2):169-175.

Birrer, M.J. et al. (2019, e-pub. Mar. 11, 2019). "Antibody-Drug Conjugate-Based Therapeutics: State of the Science," JNCI: Journal of the National Cancer Institute 111(6):538-549.

Dai, L. et al. (2022, e-pub. Mar. 16, 2022). "Efficacy of Disitamab Vedotin in Treating HER2 2+/FISH– Gastric Cancer," OncoTargets and Therapy 15:267-275.

Extended European Search Report, dated Mar. 14, 2024, for European Patent Application No. 23202349.9, 7 pages.

Hoffmann-La Roche (Aug. 28, 2019). "A Study to Determine Best Tumor Response with Trastuzumab Emtansine in Human Epidermal Growth Factor Receptor 2 (HER2) Overexpressing Solid Tumors (KAMELEON)," ClinicalTrials.gov, Identifier NCT02999672, version 17, 11 pages.

Humblebee & Me (Nov. 21, 2023). "Polysorbate 80 Emulsifiers & Solubilizers," retrieved from the Internet: https://www.humblebeeandme.com/polysorbate-80, lasted visited Nov. 21, 2023), 9 pages.

International Preliminary Report on Patentability, issued Nov. 21, 2023, for PCT Application No. PCT/CN2022/093632, filed May 18, 2022, 6 pages.

International Preliminary Report on Patentability, issued Nov. 21, 2023, for PCT Application No. PCT/CN2022/093631, filed May 18, 2022, 7 pages.

International Search Report and Written Opinion, mailed Dec. 18, 2023, for PCT Application No. PCT/CN2023/118894, filed Sep. 14, 2023, 12 pages.

International Search Report, and Written Opinion mailed Jun. 21, 2024, for PCT Application No. PCT/US2024/019136, filed Mar. 8, 2024, 15 pages.

Janjigian, Y.Y. et al. (Dec. 23-30, 2021, e-pub. Dec. 15, 2021). "KEYNOTE-811 Trial of Dual PD-1 amd JER2 B;pcladed om JER2-Positive Gastric Cancer," Nature 600:727-730 and Supplemental, 16 pages.

Janjigian, Y.Y. et al. (May 26, 2019). "KEYNOTE-811 Pembrolizumabplus Trastuzumab and Chemotherapy for HER2+ Metastatic Gastric Orgastroesophageal Junction Cancer(mF/GEJC): A Double-Blind, Randomized, Placebo-Controlled Phase 3 Study," Journal of Clinical Oncology 37(Suppl. 15): Abstract: TPS4146, 3 pages.

Kang, J. et al. (Apr. 2016). "Rapid Formulation for Development of Monoclonal Antibodies," BioProcess Technical, pp. 40-45.

Lewis, G. et al. (2024, e-pub. Jan. 11, 2024). "The HER2-Directed Antibody-Drug Conjugate DHES0815A in Advanced and/or Metastatic Breast Cancer: Preclinical Characterization and Phase 1 Trial Results," Nature Communications 15(1):466, 15 pages.

NCT04311034 (Sep. 26, 2018). "A Study of RC48-ADC in Subjects with Advanced Non-Small Cell Lung Cancer," 11 pages. (Jul. 18, 2024).

Qi, X.J. et al. (Sep. 30, 2022). "Efficacy of Distamab Vedotin in a Heavily Pre-treated HER2 Positive Lung Adenocarcinoma Patient: Case Report and Literature Review," Heliyon 8(9):e10581, 6 pages.

Rani, B. et al. (Oct. 8, 2023). "Current and Emerging Strategies to Treat Urothelial Carcinoma," Cancers 15(19):4886, 27 pages.

She, D.Y. et al. (Feb. 15, 2015). "Preparation and Biological Activity of Anti-HER2 Antibody-MMAE Conjugate," China Biotechnology 35(2):66-71. English Abstract.

Sheng, X. N. et al. (May 31, 2023). "Disitamab Vedotin, A Novel Humanized Anti-HER2 Antibody-Drug Conjugate (ADC), Combined with Toripalimab in Patients with Locally Advanced or Metastatic Urothelial Carcinoma: An Open-Label Phase 1b/2 Study," Journal of Clinical Oncology 41(Suppl. 16): 4566, 1 page.

Shi, F. et al. (2022, e-pub. May 4, 2022). "Disitamab Vedotin: A Novel Antibody-Drug Conjugates for Cancer Therapy," Drug Delivery 29(1):1335-1344.

Tan, X.L. et al. (Aug. 3, 2023). "Her-2 Promoting Tumor Progression and Cisplatin Resitance as a Novel Therapeutics Target in Penile Squamous Cell Carcinoma," JCO Global Oncology 9(Supple. 1):67, 1 page.

Anonymous (Jun. 5, 2019). "Chinese Original Research and Development of ADC Drugs Appeared on the International Stage, Brining Breakthrough in the Treatment of HER2 Positive Urothelial Carcinoma," English Translation, 10 pages.

Anonymous, Polysorbate 80 (Wikipedia, obtained from: https://en.wikipedia.org/wiki/Polysorbate 80 available as of 2013 as evidenced by Wayback Machine (2 pages).

Chen, H. et al. (2017). "Tubulin Inhibitor-Based Antibody-Drug Conjugates for Cancer Therapy," Molecules 22(1281):1-28.

Cutsem, E.V. et al. (2019). "Binimetinib, Encorafenib, and Cetuximab Triplet Therapy for Patients with BRAF V600E-Mutant Metastic Colorectal Cancer: Safety Lead-In Results from the Phase III Beacon Colorectal Cancer Study," J. Clin. Oncol. 37:1460-1469. (Aug. 19, 2025).

De Sanctis et al. "From seaside to bedside: Current evidence and future perspectives in the treatment of breast cancer using marine compounds," Frontiers in Pharmacology, vol. 13, Sep. 8, 2022, pp. 1-15.

English translation of International Search Report issued in International Application No. PCT/CN2014/091332, dated Feb. 11, 2015.

Extended European Search Report issued in European Application No. 22779052, dated Jan. 20, 2025, (11 pages).

Fan, S.M. et al. "Combination therapy with antibody-drug conjugate RC48 (disitamab vedotin) and zimberelimab (PD-1 inhibitor) successfully controlled recurrent HER2-positive breast cancer resistant to trastuzumab emtansine: A case report," Oncology letters, vol. 26, No. 2, Jul. 5, 2023 (Jul. 5, 2023), Article 359 (pp. 1-6).

Fraguas-Sanchez et al., "Actively Targeted Nanomedicines in Breast Cancer: From Pre-Clinal Investigation to Clinic," Cancers 2022, 14, 1198. https://doi.org/10.3390/cancers14051198 (33 pages).

International Search Report and Written Opinion of International Application No. PCT/CN2022/093632, dated Aug. 19, 2022, (7 pages).

International Search Report and Written Opinion issued in International Application No. PCT/US2024/042115, dated Nov. 18, 2024, (15 pages).

International Search Report and Written Opinion of International Application No. PCT/CN2022/084236, dated Jun. 28, 2022, by Y. Cui (11 pages).

International Search Report and Written Opinion, mailed Dec. 18, 2023, for PCT Application No. PCT/CN2023/118900, filed Sep. 14, 2023, 12 pages.

International Search Report and Written Opinion of International Application No. PCT/CN2023/138811, dated Aug. 28, 2024, (14 pages).

International Search Report and Written Opinion of International Application No. PCT/CN2024/139206, dated Mar. 17, 2025, 13 pages.

International Search Report and Written Opinion of International Application No. PCT/US2024/019136, dated Jun. 21, 2024, (10 pages).

International Search Report and Written Opinion of International Application No. PCT/CN2024/109209, dated Nov. 5, 2024, (13 pages).

International Search Report and Written Opinion of International Application No. PCT/CN2022/084238, dated Jun. 27, 2022, by X. Jiang (11 pages).

Qilu Hospital of Shandong University. "Study of Disitamab Vedotin and Anlotinib in Patients With HR-Negative, HER2-Low-Expressing Metastatic Breast Cancer" Aug. 21, 2023, ClinicalTrials.gov ID NCT06000033, pp. 1-9.

Jones, P.T. et al. (May 29, 1986). "Replacing the Complementarity-Determining Regions in a Human Antibody With Those From a Mouse," Nature 321:522-525.

Li, M.-R. et al. (Aug. 31, 2015). "Gene Amplification and Protein Expression of the Human Epidermal Growth Factor Receptor 2 in Urothelial Carcinoma of Bladder," J. Gannan Med. Univ., 35(4):514-517, English Abstract, 5 pages.

(56)  References Cited

OTHER PUBLICATIONS

Qi et al., "Efficacy of Disitamab Vedotin in a heavily pre-treated HER2 positive lung adenocarcinoma patient: case report and literature review," Heliyon, vol. 8, No. 9, Sep. 16, 2022, 6 pages.

Qu, F. et al. "Efficacy and safety of RC48-ADC in HER2-positive and HER2-low metastatic breast cancer: a multicenter, real-world study," Frontiers in Oncology, vol. 14, Nov. 8, 2024 (Nov. 8, 2024), Article 1435485, pp. 1-11.

Kulukian et al., Tucatinib, a HER2-Selective Tyrosine Kinase Inhibitor, Increases the Anti-tumor Activity of Trastuzumab Antibody-Drug Conjugates in Preclinical Models of HER2+ Breast Cancer, Abstract PI-18-90, San Antonio Breast Cancer Symposium, Dec. 10-14, 2019, San Antonio, Texas (1 Page).

RemeGen Co., Ltd. "DV in Combination With Pertuzumab With or Without Toripalimab Neoadjuvant Therapy With HER2-positive Breast Cancer," Dec. 11, 2023, ClinicalTrials.gov ID NCT06178159; 17 pages.

Sheng, X. et al. (Jan. 1, 2021). "Open-Label, Multicenter, Phase II Study of RC48-ADC, A HER2-Targeting Antibody-Drug Conjugate, in Patients with Locally Advanced or Metastatic Urothelial Carcinoma," Clinical Cancer Research 27(1):43-51.

Shi, F. et al. "Disitamab vedotin: a novel antibody-drug conjugates for cancer therapy," Drug delivery, vol. 29, No. 1, Dec. 31, 2022 (Dec. 31, 2022), pp. 1335-1344.

Sun Yat-Sen Memorial Hospital of Sun Yat-Sen University. "Disitamab Vedotin (RC48) in Hormone Receptor Positive, HER2-low Metastatic Breast Cancer (the Rosy Trial)" Jun. 22, 2023, ClinicalTrials. gov ID NCT05904964, pp. 1-13.

Swain et al. "Targeting HER2-positive breast cancer: advances and future directions," Nature Reviews Drug Discovery, vol. 22, Nov. 7, 2022, pp. 101-126.

Willis et al., "Disitamab Vedotin, An Investigational HER2-Directed Antibody-Drug Conjugate, Shows Potent Antitumor Activity as a Monotherapy and in Combination with Tucatinib in Preclinical Cancer Models," Abstract 560, American Association for Cancer Research Annual Meeting, Apr. 14-19, 2023, Orlando, Florida (1 page).

Wang et al. "RC48-ADC treatment for patients with HER2-expressing locally advanced or metastatic solid tumors: a real-world study," BMC Cancer, vol. 23, No. 1, Nov. 9, 2023, pp. 1-10.

Wang, K. et al. "Real-world application of disitamab vedotin (RC48-ADC) in patients with breast cancer with different HER2 expression levels: efficacy and safety analysis," The Oncologist, Nov. 16, 2024 (Nov. 16, 2024), pp. 1-11.

Wang et al., "Disitamab vedotin, a HER2-directed antibody-drug conjugate, in patients with HER2-overexpression and HER2-low advanced breast cancer: a phase I/Ib study," Cancer Communications, vol. 44, No. 7, Jun. 28, 2024 (Jun. 28, 2024), pp. 833-851.

Tonsberg et al., "Effects of polysorbate 80 on the in-vitro precipitation and oral bioavailability of halofantrine from polyethylene glycol400 formulations in rats," Journal of Pharmacy and Pharmacology, vol. 62, Issue 1, Jan. 2010, (26 pages).

European Medicines Agency, Trazimera, Retrieved from: https://web.archive.org/web/20231129060223/https://www.ema.europa.eu/en/medicines/human/EPAR/trazimera(2023) (9 pages).

Extended European Search Report issued in European Application No. 22779053.2, dated Dec. 4, 2025, (9 pages).

Invitation to Pay Additional Fees for International Application No. PCT/US2025/039221, dated Nov. 3, 2025, (16 pages).

Jiang et al., "HER2-targeted antibody drug conjugates for ovarian cancer therapy," European Journal of Pharmaceutical Sciences, 93: 274 (2016).

Miller et al., "Biosimilars for breast cancer: a review of HER2-targeted antibodies in the United States", Therapeutic Advances in Medical Oncology, 11:1 (2019).

Clinicaltrials.gov, "A Study of RC48-ADC Administered Intravenously to Patients with HER2-Positive Metastatic Breast Cancer with or without Liver Metastases" (NCT03500380) (2022) (11 pages).

Clinicaltrials.gov, "A Study of RC48-ADC for the Treatment of Locally Advanced or Metastatic Breast Cancer With Low Expression of HER2" (NCT04400695) (2021) (11 pages).

Extended European Search Report issued in European Application No. 227555489, dated Nov. 18, 2025, (12 pages).

Gogia et al., "Antibody-Drug Conjugates: a Review oprproved Drugs and Their Clinical Level of Evidence," Cancers 15: 3886 (2023).

US Food and Drug Administration, "FDA Grants Accelerated Approval to Telisotuzumab Vedotin-tllv for NSCLC with High c-Met Protein Overexpression," available at https://www.fda.gov/drugs/resources-information-approved-drugs/fda-grants-accelerated-approval-telisotuzumab-vedotin-tllv-nsclc-high-c-met-protein-overexpression (2025).

Muro et al., "Enfortumab Vedotin in Patients with Advanced Non-small Cell Lung Cancer After Disease Progression on Platinum- and PD-1/PD-L1 Inhibitor-containing Regimens: Phase 2 International Multicenter EV-202 Study," European Journal of Cancer 227: 115603 (2025).

Rohrberg et al., "Phase I/II Study of AXL-specific Antibody-drug Conjugate Enapotamab Vedotin in Patients with Advanced Solid Tumors," Cancer Research Communications 5(11): 2067 (2025).

Sheng et al., "Efficacy and Safety of Disitamab Vedotin in Patients with Human Epidermal Growth Factor Receptor 2-Positive Locally Advanced or Metastatic Urothelial Carcinoma: a Combined Analysis of Two Phase II Clinical Trials," Journal of Clinical Oncology 42(12): 1391 (2023).

* cited by examiner

1

USE OF ANTI-HER2 ANTIBODY-DRUG CONJUGATE IN TREATING UROTHELIAL CARCINOMA

CROSS-REFERENCE TO RELATED APPLICATIONS

The present application is a U.S. National Phase application based upon PCT Application No. PCT/CN2019/101283, filed Aug. 19, 2019, which claims priority to Chinese Patent Application No. 201810998055.4, filed Aug. 29, 2018, and the disclosures of both of which are hereby incorporated by reference in their entireties.

TECHNICAL FIELD

The present disclosure relates to use of an anti-HER2 (human epidermal growth factor receptor 2) antibody-drug conjugate in the treatment of urothelial carcinoma.

BACKGROUND

Urothelial carcinoma (UC; also known as transitional cell carcinoma, TCC) is a type of carcinoma that is usually found in the urinary system, such as kidney, bladder, and accessory organs. It is the most common type cancer among bladder carcinoma and carcinoma of ureter, urethra or umbilical duct. It is also the second most common type of renal carcinoma, accounting for 5-10% of all primary renal malignant tumors.

Urothelium (also called transitional epithelium) is the lining of the bladder, the ureter, and the inside of the urethra, and the renal pelvis (the part of the kidney where urine is collected). It is composed of urothelial cells or transitional cells. These cells can develop into cancer cells, known as urothelial carcinoma (or transitional cell carcinoma).

Depending on the invasiveness of the cancerous cells, urothelial carcinoma can be non-invasive (only in the lining of the bladder) or invasive (growing into other layers of the bladder wall). Among them, non-invasive urothelial carcinoma is only in the bladder endometrium and does not grow deeper into the bladder wall. At the time of diagnosis, 50%-60% of patients with urothelial carcinoma are non-invasive. Types of non-invasive urothelial carcinoma include: non-invasive flat urothelial carcinoma (also known as carcinoma in situ); non-invasive papillary urothelial carcinoma, high-grade; non-invasive papillary urothelial carcinoma, low-grade malignancy; the likelihood of non-invasive papillary urothelial tumors with low malignant potential developing into aggressive cancer is low.

In contrast, invasive urothelial carcinoma grows from the lining of the bladder into the deeper layers of the bladder wall, such as connective tissue (known as the lamina propria) and muscle layer. At the time of diagnosis, the tumors in 40%-50% of patients with urothelial carcinoma are invasive.

In theory, urothelial carcinoma can originate from any part of the urinary tract, including but not limited to the renal pelvis, ureter, bladder and urethra.

Before metastasis happens from relevant tumor cells, surgical resection is the preferred treatment regime. For patients with tumors that have metastasized, anti-cancer drugs are generally required. The current first-line therapy is: combination therapy of gemcitabine and cisplatin. Radiation therapy is not ideal for urothelial carcinoma and generally used as an adjuvant therapy. When treating cancer in the renal pelvis/ureter epithelium, BCG injection therapy (injection of *Mycobacterium Bovis* via catheter) may be an option.

Urothelial carcinoma is multi-centered and relapse-prone. For patients with tumors involving the muscle layer, total bladder resection is preferred, and strict re-examination is required after surgery. Therefore, treatment is difficult and the recurrence rate is high. (Li Xuesong, Wang Gang, Zhang Ye, eds. Essence of Urology Cases, Peking University Medical Press, 2017). The administration of mitomycin (a chemotherapeutic agent) to the bladder as a one-time dose early in the postoperative period (within 24 hours) or as a six-dose regimen a few weeks after surgery is also an option for some patients. Cisplatin-based chemotherapy is still the golden standard for treating patients with metastatic UC. The overall response rate (ORR) of cisplatin-based chemotherapy is 60-70%, overall survival (OS) is 14-15 months, and 5-year survival rate is 13-15%. Platinum-based chemotherapy was performed in relapsed patients with an ORR of approximately 15% and a median OS of approximately 7 months.

Vinflunine has been approved in Europe for the treatment of advanced urinary epithelial or metastatic TCC (Bellmunt, J. et al., J Clin. Oncol. 27 (27): 4454-4461 (2009)). Several agents have been tested for monotherapy and shown moderate activity, with median survival of 5 to 10 months (Yafi, F. A. et al. Current Oncol. 18 (1): e25-e34 (2011)). In metastatic cases, Docetaxel is administered as a relief option to patients with transitional cell carcinoma (NCCN 2014), and the medical communities in the United States and Canada have proved docetaxel treatment for advanced disease based on evidence from a phase 2 study (WO2016/064649A1).

In recent years, new drugs for the treatment of urothelial carcinoma mainly include: 1. Atezolizumab from Roche (2016) is approved to be the first anti-PD-L1 cancer immunotherapy on the market. Results of the latest phase III clinical trial (IMvigor211) of Atezolizumab for locally advanced or metastatic urethral bladder cancer show that Atezolizumab failed to meet the primary clinical endpoint of the phase III trial IMvigor211, which is to improve overall survival (OS) in second-line treatment for patients with locally advanced or metastatic urothelial carcinoma (mUC). Among a total of 234 patients (116 in the Atezolizumab group and 118 in the chemotherapy group), the median overall survival was 11.1 months in the Atezolizumab group and 10.6 months in the chemotherapy group. The rate of confirmed objective responses in these evaluable patients was 23% and 22%, and the median duration of response was 15.9 months and 8.3 months, respectively.

The median progression-free survival in this group was 2.4 months, while 4.2 months in the control. In the exploratory analysis of the intention-to-treat population, the 12-month overall survival data is that: Atezolizumab was 39.2% and chemotherapy was 32.4%; median overall survival was 8.3 months for Atezolizumab, 7.5 months for taxane, and 9.2 months for vinflunine. (The ASCO Post, IMvigor211 Trial: Atezolizumab vs Chemotherapy in Platinum-Treated Advanced Urothelial Carcinoma, Matthew Stenger, Sep. 17, 2018)

In addition, the U.S. Data Surveillance Commission has observed a decrease in survival of patients with PD-L1 low-expression tumors using Atezolizumab monotherapy compared with platinum-based chemotherapy. Therefore, in June 2018, the U.S. FDA issued a restriction on the use of Atezolizumab (Tecentriq) in patients with locally advanced or metastatic urothelial cancer, who is suitable for cisplatincontaining chemotherapy. It is required to detect PD-L1 expression before using Atezolizumab. This further illustrates the limitations of Atezolizumab in the treatment of urothelial cancer.

2. Nivolumab from Bristol-Myers Squibb (2017) has been approved by the FDA for patients with locally advanced or metastatic urothelial carcinoma. Nivolumab is an anti-PD-1 monoclonal antibody. Clinical data show that Nivolumab's objective response (ORR) was 19.6% and median overall survival rate was 8.7 months. The most common serious adverse events include: urinary tract infection, sepsis, diarrhea, small bowel obstruction, and deterioration of overall health status. Nivolumab treatment was discontinued in 17% of patients due to adverse reactions, and administration of Nivolumab in 46% of patients was delayed due to adverse reactions. In clinic practice, treatment-related deaths were seen in 3 patients due to pneumonia or cardiovascular failure.

Based on the above, the main problem of PD-L1/PD-1 immunotherapy drugs in the current clinical stage is the poor treatment effect, which is mainly reflected in the treatment data such as objective response rate (ORR) and median overall survival, are not ideal. Another major problem is the relatively high proportion of serious adverse effects. For example, Nivolumab caused 3 deaths in related clinical trials.

3. Erdafitinib from Janssen (a Johnson & Johnson company) was granted breakthrough drug qualification by the FDA in 2018 for the treatment of patients with locally advanced or metastatic urothelial cancer who have progressed after chemotherapy and whose tumor has specific fibroblast growth factor (FGFR) gene changes. The drug is a fibroblast growth factor receptor (FGFR) tyrosine kinase inhibitor. The results of the second-phase clinical study (BLC2001, NCT02365597) showed that the overall response rate of erdafitinib treatment was 40% (complete response rate 3%, partial response rate 37%), the median progression-free survival was 5.5 months and overall survival time was 13.8 months. Out of a total of 99 patients, 7 patients discontinued due to treatment-related adverse events. Data from "Erdafitinib Phase 2 Study Results Show Promise in the Treatment of Metastatic Urothelial Cancer" Press Release dated Jun. 3, 2018 available at jnj.com. Because the therapeutic target of this drug is FGFR, it is only suitable for patients with urothelial cancer who have certain FGFR gene mutations, while FGFR is only overexpressed in 15% to 20% of metastatic urothelial cancer and 40% to 70% of non-muscle invasive bladder cancer (2018 ASCO Annual Meeting, Responses Found in Advanced Urothelial Carcinoma with FGFR Inhibitor).

The current treatment results shown that advanced urothelial carcinoma has a high degree of malignancy and a poor prognosis. Especially after the failure of conventional chemotherapy, the treatment options are limited. Immunotherapy can only benefit some patients. Moreover, the number of available immunotherapeutic inhibitors is also very limited, the objective response rate is not high, the side effects of treatment are large, or there are specific genetic requirements. At present, there are not many therapeutic drugs that can be choose by patients. Therefore, it is still necessary to develop drugs with more significant therapeutic effects and wider application to meet the urgent clinical needs.

SUMMARY

The present disclosure provides a method for treating urothelial carcinoma. The method comprises injecting an effective amount of an antibody-drug conjugate (ADC) into a patient, wherein the ADC is an anti-HER2 antibody conjugated cytotoxic molecule. The cytotoxic molecule includes, but is not limited to, a tubulin inhibitor or a DNA damaging agent. The tubulin inhibitor includes, but is not limited to, dolastatin and derivatives thereof, auristatin and derivatives thereof, and maytansine and derivatives thereof; the DNA damaging agents include, but are not limited to calicheamicins, duocarmycins, anthramycin derivative PBD (pyrrolobenzodiazepine), and camptothecin derivative SN-38. The auristatin and derivatives thereof include, but are not limited to, monomethyl auristatin E (MMAE), monomethyl auristatin F (MMAF), auristatin F (AF) or derivatives thereof; the maytansine and derivatives thereof include, but are not limited to, DM1, DM3, DM4 and derivatives thereof (Research progress of bullet molecules of antibody-drug conjugates, Hu Xinyue et al., Chin Med Biotechnol, December 2017, Vol. 12, No. 6) (Research progress of maytansinoid antibody drug conjugates, Zhou Lei et al., Chinese Journal of New Drugs, Volume 25, Issue 22, 2521-2530). The cytotoxic molecules may also be amanitins, anthracyclines, baccatins, camptothecins, cemadotins, colchicines, colcimids, combretastatins, cryptophycins, discodermolides, docetaxel, doxorubicin, echinomycins, eleutherobins, epothilones, estramustines, lexitropsins, maytansines, methotrexate, netropsins, puromycins, rhizoxins, taxanes, tubulysins, or vinca alkaloids. The cytotoxic molecules are not limited to the above-mentioned categories, and may include all drugs that can be used for ADC.

Another aspect of the present disclosure is to provide an antibody-drug conjugate (ADC) for use in the manufacture of a medicament for treating bladder cancer. The antibody-drug conjugate comprises an antibody or a functional fragment thereof capable of binding to HER2, wherein the antibody comprises a heavy chain variable region and a light chain variable region, and wherein (i) the heavy chain variable region comprises three CDRs, wherein the CDRs have amino acid sequences of SEQ ID NO: 1, 2 and 3, respectively; and (ii) the light chain variable region comprises three CDRs, wherein the CDRs have the amino acid sequences of SEQ ID NO: 4, 5 and 6, respectively. The antibody may also be an antibody capable of competing with a defined antibody against the same or similar epitope, wherein the defined antibody comprises the above CDRs.

In the present disclosure, the term "antibody" may include a full-length antibody or an antibody fragment that binds to, reacts with, or composites with HER2. An antibody can be any protein, protein-like molecule, or polypeptide that binds, composites, or reacts with a portion of a population of cells seeking therapeutic modification. The antibody may be a chimeric antibody or a functionally active fragment thereof, a humanized antibody or a functionally active fragment thereof, a human antibody or a functionally active fragment thereof. It can also be an antibody or a functionally active fragment thereof of derives from another species other than the above species, for example: mouse antibody or functionally active fragment thereof, rat antibody or functionally active fragment thereof, goat antibody or functionally active fragment thereof, rabbit antibody or functionally active fragment thereof. The antibody may be a polyclonal antibody or a monoclonal antibody. In some embodiments, the antibody may be a bispecific antibody. Also, the antibody may be a functionally active fragment, a derivative or analog of the antibody. "Functionally/functional" means that the fragments, derivatives, or analogs can recognize the same antigen, and the antibodies that can recognize fragments, derivatives, or analogs derived from the antigen, such as but not limited to: F (ab')$_2$, Fab, Fab', Fv fragments and dimers of antibody heavy chains and light chains, or any minimal fragments thereof, like Fvs or single chain antibodies (SCAs). In addition, the antibody may be a fusion protein of an antibody. Antibodies may also include analogs and derivatives that are modified or unmodified (i.e., covalently linked to any molecule), as long as such covalent bonding allows the antibody to retain its antigen-binding immunospecificity. Examples include, but are not limited to, analogs and derivatives of antibodies, including further modifications such as: glycosylation, acetylation, pegylation, phosphorylation, amidation, derivatization via known protecting/blocking groups, protease cleavage, attachment to cellular antibody units or other proteins, and the like. Any bulk chemical modifications can be achieved using known techniques, including but not limited to specific chemical cleavage, acetylation, formylation, metabolic synthesis in the presence of tunicamycin, and the like. In addition, analogs or derivatives may include one or more unnatural amino acids. In some embodiments, the antibody may have modifications (e.g., substitutions, deletions, or additions) in amino acid residues that interact with the Fc receptor. In another aspect, the antibody-drug conjugate has a structure represented by formula Ab-(L-U)n, wherein Ab is the antibody or a functional fragment thereof, L is a linker, U is a coupled cytotoxic molecule, n is an integer from 1 to 8, representing the number of therapeutic agent molecules bound to the antibody.

In another aspect, the linker is linked to the antibody or the functional fragment thereof via a thiol group and/or an amino group, and the cytotoxic molecule is conjugated to the antibody through site-directed or undirected conjugation. The linker of the present disclosure may be selected from the following table:

6

The linker of the present disclosure is preferably Maleimido-Caproyl-Valine-Citrulline-p-Aminobenzyloxy (mc-vc-pAB) and Maleimidocaproyl (mc).

The linker of the present disclosure may also be triglycyl peptide linker, which is a new linker for ADCs developed in recent years (Rajeeva Singh et al., A New Triglycyl Peptide Linker for Antibody-Drug Conjugates (ADCs) with Improved Targeted Killing of Cancer Cells, MCT-16-002, Published June 2016). Alternatively, a glucuronide-tubulysin linker can be used (Patrick J. Burke et al., Glucuronide-linked antibody-tubulysin conjugates display activity in MDR$^+$ and heterogeneous tumor models, Molecular Cancer Therapeutics, 2018).

In another aspect, the antibody or the functional fragment thereof is derived from an antibody secreted by the hybridoma deposited at the China General Microbiological Culture Collection Center of China Committee for Culture Collection of Microorganisms, with an accession number CGMCC No. 8102 on Aug. 22, 2013.

In another aspect, the antibody is a humanized antibody, preferably, the antibody is an antibody secreted by CHO cells deposited at the China Center for Type Culture Collection under the accession number CCTCC C2013170 on Nov. 6, 2013.

In an embodiment, the antibody-drug conjugate used is named RC48-mc-vc-pAB-MMAE, which conforms to the structure of the general formula Ab-(L-U)n, in which RC48 (a humanized anti-HER2 monoclonal antibody) is coupled to MMAE through the linker mc-vc-pAB, and the number of coupling ranges from 1 to 8, including 1, 2, 3, 4, 5, 6, 7, 8 or a combination of antibody-drug conjugates with varying MMAE coupling numbers ranging from 1 to 8.

In the present disclosure, the urothelial carcinoma is locally advanced urothelial carcinoma that cannot be removed by surgery, locally advanced or metastatic urothelial carcinoma, HER2 (Human Epidermal Growth Factor Receptor 2, also called ErbB-2, C-erbB2, or HER2/neu)

| Abbreviation | Full name | Feature |
|---|---|---|
| mc | Maleimidocaproyl | Non-cleavable [12] |
| mc-vc-pAB | Maleimidocaproyl valine citrulline p-amino-benzyl | Cleavable[12] |
| 3-MPA | 3-maleimido-propionic acid | Non-cleavable [12] |
| Mal-di-EG-OPFP | Perfluorophenyl 3-(2-(2-(3-(2,5-dioxo-2,5-dihydro-1H-pyrrol-1-yl)propanamido)ethoxy)ethoxy)propanoate | Non-cleavable [14] |
| Mal-di-EG-OSu | 2,5-dioxopyrrolidin-1-yl 3-(2-(2-(2,5-dioxo-2,5-dihydro-1H-pyrrol-1-yl)ethoxy)ethoxy)propanoate | Non-cleavable [14] |
| Mal-Tri-EG-OSu | 2,5-dioxopyrrolidin-1-yl 3-(2-(2-(2-(2,5-dioxo-2,5-dihydro-1H-pyrrol-1-yl)ethoxy)ethoxy)ethoxy)propanoate | Non-cleavable [14] |
| Mal-Tetra-EG-OSu | 2,5-dioxopyrrolidin-1-yl 1-(2,5-dioxo-2,5-dihydro-1H-pyrrol-1-yl)-3-oxo-7,10,13,16-tetraoxa-4-azanonadecan-19-oate | Non-cleavable [14] |
| Br-di-EG-OSu | 2,5-dioxopyrrolidin-1-yl 3-(2-(2-(2-bromoacetamido)ethoxy)ethoxy)propanoate | Non-cleavable [14] |
| Py-ds-prp-OSu | 2,5-dioxopyrrolidin-1-yl 3-(pyridin-2-yldisulfanyl)propanoate | Reducible [14] |
| Py-ds-Prp-OPFP | Perfluorophenyl 3-(pyridin-2-yldisulfanyl)propanoate | Reducible [14] |
| Py-ds-dmBut-OSu | 2,5-dioxopyrrolidin-1-yl 4-methyl-4-(pyridin-2-yldisulfanyl)pentanoate | Reducible [14] |
| Py-ds-dmBut-OPF | Perfluorophenyl 4-methyl-4-(pyridin-2-yldisulfanyl)pentanoate | Reducible [14] |
| SMCC | N-succinimidyl 4-(maleimidomethyl) cyclohexanecarboxylate | Non-cleavable [13] |
| MBS | 3-maleimidobenzoic acid N-hydroxysuccinimide ester | Non-cleavable [13] |
| SATA | S-(N-succinimidyl) thioacetate | Non-cleavable [13] |
| SPDP | N-succinimidyl 3-(2-pyridyldithio)propionate | Reducible [13] |
| SMPT | (N-succinimidyl carbonyl)-1-methyl-1-(2-pyridyldithio) toluene | Reducible [13] | positive urothelial carcinoma, HER2 positive locally advanced or metastatic urothelial carcinoma.

The medicament described in the present disclosure may be administered intranasally, subcutaneously, intradermally, intramuscularly, or intravenously. The medicament also includes a pharmaceutically acceptable carrier; the medicament is preferably a lyophilized formulation or a liquid formulation; the carrier comprises one or more selected from the group consisting of a stabilizer, a protective agent, a buffer, a lyoprotectant, an activity protective agent, a surfactant and an adsorption carrier and an absorption promoter.

DETAILED DESCRIPTION OF THE INVENTION

Example 1. Preparation and Sequence Analysis of Murine Monoclonal Antibody mRC48

1. Expression and Purification of HER2 Antigen

The cDNA fragment encoding HER2-ECD (from Thr23 to Thr652, GenBank accession No. M11730) was cloned into pcDNA3 expression vector (Invitrogen) by PCR.

The detailed method: the cDNA of HER2-ECD coding region was obtained from HER2$^+$ SKBR3 cell line (ATCC No. HTB-30) by RT-PCR (using ImProm-II™ Reverse Transcription System of Promega).

Figure 1:
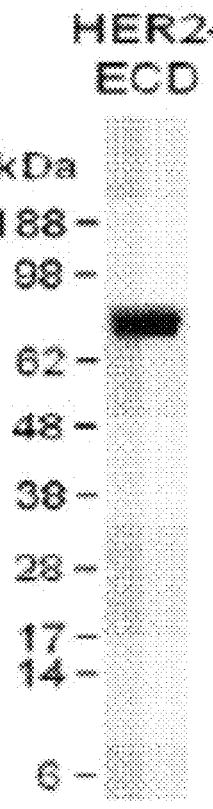
FIG. 1: SDS-PAGE of purified human recombinant protein HER2-ECD, stained by Coomassie brilliant blue. The loading amount was 10 µg per lane.

The primers are:

```
P1:
                                      (SEQ ID NO: 7)
  5'CGGGATCCTGCCACCAGCTGTGCGCC,
P2:
                                      (SEQ ID NO: 8)
  5'GCTCTAGA TCAGTTGATGGGGCAAGGCT,
``` the underlined sequences are the introduced BamHI and XbaI restriction enzyme cutting sites, respectively. The HER2-ECD cDNA obtained by reverse transcription was used as a template for PCR amplification using the above primers. The amplification conditions: denaturing at 94° C. for 30 s, annealing at 60° C. for 30 s, extending at 72° C. for 1 minute, for a total of 30 cycles, and then extending at 72° C. for 10 minutes. The PCR fragment was then recovered, digested with BamHI and XbaI (from NEB), and ligated with pcDNA3 vector. A polyhistidine tag was added to the C-terminus of HER2-ECD to facilitate purification. HEK293 cells (ATCC, USA) were transfected with the constructed DNA expression vector, and soluble protein HER2-ECD with his-tag was purified from the culture medium by Ni-NTA affinity chromatography (Qiagen). SDS-PAGE and Coomassie brilliant blue staining showed that the purified HER2-ECD protein had more than 95% homogeneity, as shown in FIG. 1. Soluble HER2-ECD appears as a monomer with a relative molecular weight of about 75 kDa, slightly larger than the calculated molecular weight (71 kDa), indicating the protein was glycosylated in HEK293 cells. The purified HER2-ECD protein was further concentrated and transferred to a sterile pH 7.4 PBS buffer for subsequent in vivo and in vitro analysis.

2. Generating and Screening of Hybridoma Cells

Mice were immunized with the HER2-ECD prepared above as the antigen to produce antibodies. Immunization, hybridoma cell fusion, and preliminary screening were performed according to standard procedures (Reference: WHO Technical Report Series, No. 822, 1992 Annex 3). 0.25 mL of HER2-ECD protein (50-100 µg) and 0.25 ml of Freund's complete adjuvant (Difco Lab) were mixed in equal volume and used to immunize 4 Balb/c mice (purchased from Shanghai SLAC Laboratory Animal Co., Ltd). The second injection was performed after 2 weeks. Freund's incomplete adjuvant (Difco Lab) and antigen with the amount of 25-50 µg/0.5 mL/per mouse were used for the second injection. 3 weeks after, the third injection was performed at the same dose as that of the second injection. Blood was taken 10 days after the third injection. The serum of the mice was analyzed by enzyme-linked immunosorbent assay (ELISA). The cells from the spleens of the two mice with the highest anti-HER2 antibody titers were taken, and then fused with myeloma cells P3X63Ag8 (ATCC, CRL-1580). The fused cells were diluted into 96-well plate, and screened preliminarily by ELISA according to the binding ability with HER2-ECD. In a typical ELISA, Nunc Maxisorb 96-well plate was coated with HER2-ECD (0.2-1 µg/mL) and then incubated with a gradient dilution of mouse serum or hybridoma supernatant (100 µL). The mouse anti-HER2 antibody was detected using a horseradish peroxidase-conjugated goat F(ab')$_2$ anti-mouse IgG Fc (Invitrogen) secondary antibody.

ELISA was used to screen the supernatants of 400 hybridoma cell lines, of which 36 showed strong binding with HER2-ECD. Ten hybridoma cells with the strongest HER2 binding ability were selected and subcloned hybridoma cell lines were screened again by limiting dilution method. The subcloned hybridoma cell lines were cultured in suspension, proteins were purified, and the binding affinity with HER2 was determined by ELISA. The binding ability of the above antibodies to HER2 expressed on the surface of human breast cancer cell lines was further tested by flow cytometry (BD FACS Calibur) (see Example 4 for detailed description). Finally, a hybridoma cell line mRC48 (murine IgGlk) was identified through sequence analysis, which has strong HER2 binding capacity. The hybridoma cell mRC48 was deposited with accession No. 8102 at China General Microbiological Culture Collection Center of China Committee for Culture Collection of Micro-organisms on Aug. 22, 2013 (the date of conversion to deposit under the Budapest Treaty was Oct. 29, 2013).

3. Sequence Analysis of Anti-HER2 Antibody from Hybridoma Cell Clone mRC48

The 5' ends of the heavy chain and light chain variable regions of clone mRC48 were rapidly amplified using the commercial SMART™ RACE cDNA Amplification Kit (Clontech) for sequencing according to the instructions.

Total RNA was extracted from hybridoma cells using RNApure Tissue Kit (Beijing ComWin Biotech Co., Ltd), and reverse transcription was performed using the SMART™ RACE cDNA Amplification Kit. First-strand cDNA for RACE-Ready was obtained by reverse transcription according to the protocol provided with the kit, using the total RNA as the template, the primers provided with the kit, and reverse transcriptase SMARTScribe™ Reverse Transcriptase. And then two rounds of PCR were carried out. For the first round PCR, the obtained cDNA was as template, the UPM provided with the kit was used as the 5 'end primer and mRC48-VL-1/mRC48-VH-1 as the 3' end primer. The PCR reaction conditions: pre-denaturation at 94° C. for 5 minutes; 25 cycles (denaturation at 94° C. for 30 s, annealing at 68° C. for 30 s and extension at 72° C. for 2 minutes); and extension at 72° C. for 10 minutes.

The second round PCR was performed using the products of the first round PCR as the template, NUP15 provided with the kit as the 5' end primer and mRC48-VL-2/mRC48-VH-2 as the 3' end primer. PCR reaction conditions: pre-denaturation at 94° C. for 5 min; 25 cycles (denaturation at 94° C. for 30 s, annealing at 68° C. for 30 s and extension at 72° C. for 2 min); extension at 72° C. for 10 min. Both the heavy chain and light chain variable regions of the aforementioned antibody from hybridoma cell clone mRC48 were obtained.

The primers are as follows:

```
mRC48-VL-1:
                            (SEQ ID NO: 9)
5'-GTTGGTGCAGCATCAGCCCGTT-3';

mRC48-VL-2:
                            (SEQ ID NO: 10)
5'-GTTCACTGCCATCAATCTTCCAC-3';

mRC48-VH-1:
                            (SEQ ID NO: 11)
5'-GCCAGTGGATAGACAGATGG-3';

mRC48-VH-2:
                            (SEQ ID NO: 12)
5'-AGGTCACTGTCACTGGCTCAG-3'.
```

The PCR products were purified by agarose gel electrophoresis and then subcloned into the pCR2.1TOPO cloning vector (Invitrogen). Plasmid DNAs from ten independent clones were obtained by PCR, and then sequenced using M13 forward and reverse primers. DNA sequence analysis showed that all 10 clones had cDNA encoding the same VH or VL polypeptide. The amino acid sequences of the complementarity determining regions (CDRs) are analyzed by Kabat coding table and listed in Table 1. Sequence comparison analysis showed that the CDRs of anti-HER2 mRC48 were significantly different from that of the known HER2 antibodies including Herceptin (trastuzumab).

TABLE 1

| Amino acid sequences of the CDRs of anti-HER2 monoclonal antibody mRC48 | | |
|---|---|---|
| | VH | VL |
| CDR1 | DYYIH (SEQ ID NO: 1) | KASQDVGTAVA (SEQ ID NO: 4) |
| CDR2 | RVNPDHGDSYYNQKFKD (SEQ ID NO: 2) | WASIRHT (SEQ ID NO: 5) |
| CDR3 | ARNYLFDHW (SEQ ID NO: 3) | HQFATYT (SEQ ID NO: 6) |

Example 2. Humanization of the Anti-HER2 Monoclonal Antibody mRC48 (Method as Described in CN105008398A)

Murine anti-HER2 monoclonal antibody mRC48 was humanized by transplanting light chain or heavy chain CDRs into human IgG1κ framework regions.

The humanized RC48 antibody light chain variable region (RC48-VL) and the humanized RC48 antibody heavy chain variable region (RC48-VH) were designed and constituted the humanized anti-HER2 antibody: RC48. The similarity between the overall sequence of RC48-VH and human IgG1VH is 84%. The RC48 antibody comprises a light chain variable region RC48-VL and a heavy chain variable region RC48-VH.

Humanized anti-HER2 monoclonal antibody RC48 was obtained by CDR grafting. The nucleic acid sequences of heavy chain and light chain variable regions were directly synthesized by Nanjing GenScript Biotech Corporation. The synthetic variable region comprises Kozak consensus sequence, start codon, heavy chain or light chain signal peptide, human framework region and murine CDRs. Variable regions and human IgGlk constant region were ligated into a complete fragment by overlap-extension PCR.

The primers for overlap-extension PCR:

```
Heavy chain VH1:
                            (SEQ ID NO: 13)
5' CGCGGATCCGCCGCCACCATGGGATGGAGCT 3'

VH2:
                            (SEQ ID NO: 14)
5' GATGGGCCCTTGGTGCTAGCGGAGCTCACTGTCACCAGTGTT 3'

CH1:
                            (SEQ ID NO: 15)
5' GCTAGCACCAAGGGCCCATC 3'

CH2:
                            (SEQ ID NO: 16)
5' CCGGAATTCTTTACCGGGAGACAGGGAGA 3'

Light chain VL1:
                            (SEQ ID NO: 17)
5' CGCGGATCCGCCGCCACCATGGACATGAGGGT 3'

VL2:
                            (SEQ ID NO: 18)
5' GATGGTGCAGCCACAGTACGCTTTATCTCAACTTTTGTAC 3'
```

-continued

CL1:

(SEQ ID NO: 19)

5' CGTACTGTGGCTGCACCAT 3'

CL2:

(SEQ ID NO: 20)

5' CCGGAATTCACACTCTCCCCTGTTGAAGC 3'

For the generation of heavy chain nucleic acid, first, the heavy chain variable region was amplified using the synthetic variable region as the template and VH1 and VH2 as the primers, meanwhile, human IgG1κ heavy chain constant region was used as the template and CH1 and CH2 as the primers to amplify the heavy chain constant region. The amplification conditions are: denaturation at 94° C. for 30 s, annealing at 60° C. for 30 s, extension at 72° C. for 1 minute, 30 cycles, and extension at 72° C. for 10 minutes. Then the heavy chain sequence of RC48 was amplified using the above two PCR products as the template and VH1 and CH2 as primers. The amplification conditions were: denaturation at 94° C. for 30 s, annealing at 60° C. for 30 s, extension at 72° C. for 2 minutes, 30 cycles, and extension at 72° C. for 10 minutes.

For the generation of light chain nucleic acid, first, the light chain variable region was amplified using the synthetic variable region as the template and VL1 and VL2 as the primers, meanwhile, the human IgG1κ light chain constant region was used as the template and CL1 and CL2 as the primers to amplify the light chain constant region. The amplification conditions were: denaturation at 94° C. for 30 s, annealing at 60° C. for 30 s, extension at 72° C. for 1 minute, 30 cycles, and extension at 72° C. for 10 minutes. Then the light chain sequence of RC48 was amplified using the above two PCR products as the template and VL1 and CL2 as primers. The amplification conditions were: denaturation at 94° C. for 30 s, annealing at 60° C. for 30 s, extension at 72° C. for 2 minutes, 30 cycles, and extension at 72° C. for 10 minutes.

Thus, the humanized anti-HER2 monoclonal antibody RC48 sequence was obtained, wherein RC48 comprises human IgG1κ heavy chain constant region and heavy chain variable region RC48-VH, and human IgG1κ light chain constant region and light chain variable region RC48-VL.

Human-mouse chimeric antibody cRC48 was also obtained by the same method. The murine variable region and human IgGlk constant region were ligated into a complete sequence by overlap-extension PCR.

Figure 2:
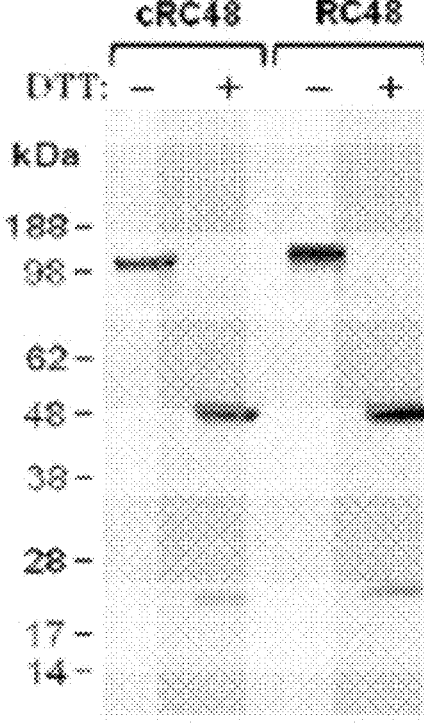
FIG. 2: SDS-PAGE analysis of cRC48 (chimeric antibody) and RC48 (humanized antibody). The loading amount was 2 µg per lane.

Each of the amplified fragments was subcloned into the expression vector pcDNA3.0, respectively. The obtained constructs were transfected into suspension CHO cells (Invitrogen) to produce different recombinant antibodies. The antibodies were purified by Protein A and subjected to subsequent characterization. Chimeric anti-HER2 RC48 (referred to as cRC48) comprises mouse-human chimeric heavy chain and light chain. RC48 comprises the humanized heavy chain RC48-VH and the humanized light chain RC48-VL. Both cRC48 and RC48 can be expressed in cells. The antibodies were collected from the supernatants of CHO cells, purified by Protein A, and analyzed by SDS-PAGE under reducing and non-reducing conditions (see FIG. 2). The CHO cells capable of secreting RC48 antibody as described above (i.e., CHO cells transfected with human IgG1κ heavy chain constant region and heavy chain variable region RC48-VH, and human IgG1κ light chain constant region and light chain variable region RC48-VL) was deposited at the China Center for Type Culture Collection on Nov. 6, 2013 with the accession number C2013170.

Example 3. Characterization of Anti-HER2 RC48 Antibody

Figure 3:
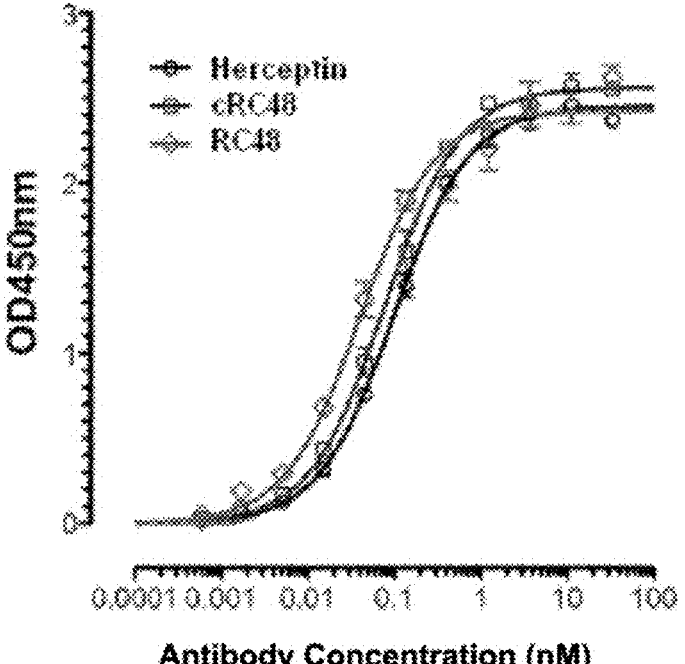
FIG. 3 shows the binding affinity of humanized antibody RC48 with HER2-ECD determined by ELISA, and the binding affinity constant Kd was calculated. Herceptin and cRC48 were used as controls in this experiment.

HER2-binding affinity constant (Kd) of cRC48 (chimeric antibody) and RC48 antibody (humanized antibody) was measured by ELISA. The specific method can be seen in Example 1. Briefly, a 96-well plate was coated with soluble HER2-ECD, followed by incubating with diluted antibodies (Herceptin and chimeric cRC48 as controls), and HRP-conjugated goat F(ab)$_2$ anti-human IgG Fc (Invitrogen) was used as the specific secondary antibody to detect HER2-ECD-related antibodies (all forms of human IgG1κ). The surface binding affinity constant (Kd) value for each anti-HER2 antibody was calculated by drawing a binding curve and further using a single-site specific binding nonlinear equation (Journal of Immunological Methods, 270: 155-162, 2002) (FIG. 3 shows a typical HER2-binding curve obtained from three independent ELISA assays). The results of the ELISA are shown in FIG. 3.

From three independent assays, it can be seen that RC48 (humanized antibody) shows an average affinity constant of 44 pM, indicating significantly improved HER2-ECD binding affinity compared to cRC48 (average affinity constant 77 pM) and Herceptin (average affinity constant 97 pM). The results are shown in Table 2.

TABLE 2

| Comparison of average affinity constant between antibodies of this invention and Herceptin | |
| --- | --- |
| Sample | Average affinity constant |
| Herceptin | 97 pM |
| cRC48 | 77 pM |
| RC48 | 44 pM |

Example 4. Binding Affinity of RC48 (Humanized Antibody) to HER2

1) Test for the Binding Affinity of RC48 Antibody to HER2

Figure 4A:
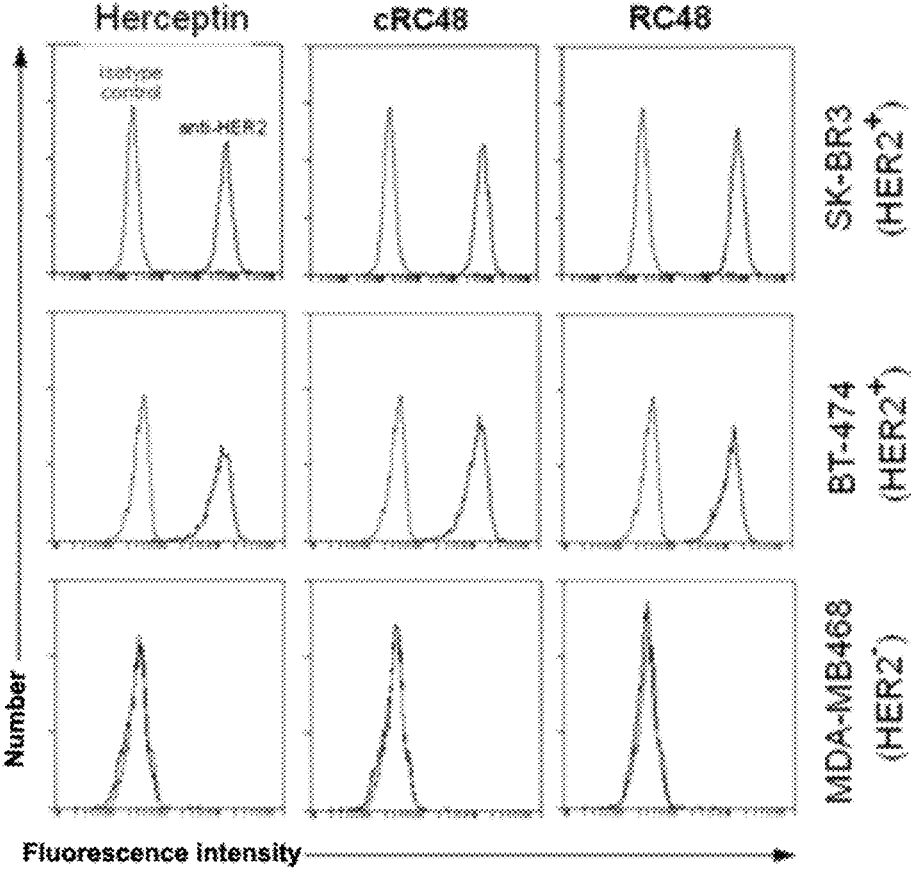
FIG. 4A shows the binding ability of the anti-HER2 humanized antibody RC48 to HER2$^+$ cells SK-BR3, BT474 and HER2$^-$ cell MDA-MB468 by flow cytometry.
Figure 4B:
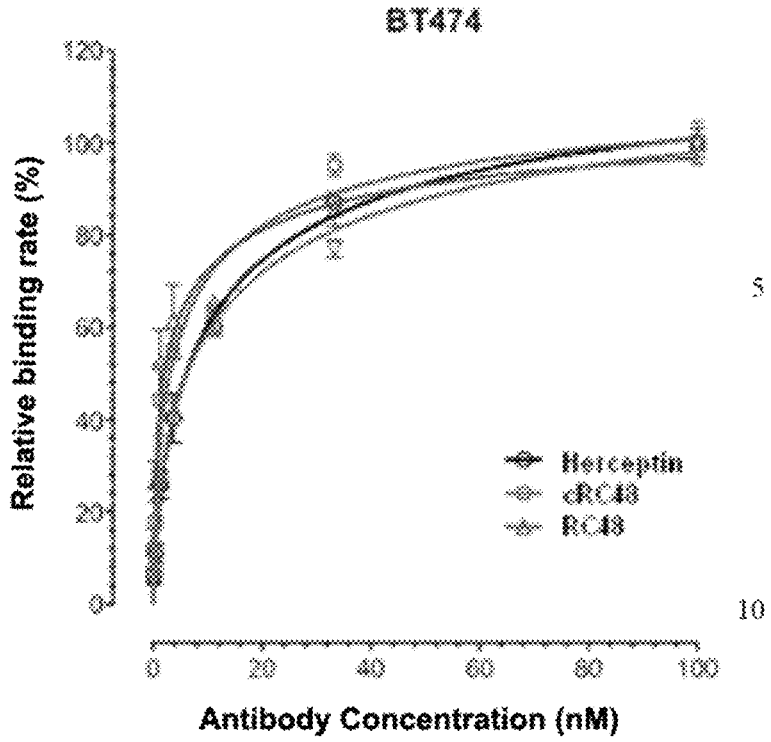
FIG. 4B shows the binding ability of anti-HER2 antibodies to BT474 cell surface antigens at different antibody concentrations by flow cytometry analysis. The anti-HER2 antibodies are Herceptin, cRC48, and RC48. A total of 5×10$^4$ cells were analyzed.

Flow cytometry was used to detect the binding affinity of endogenously expressed HER2 in human breast cancer cells with the humanized anti-HER2 antibody RC48. The results are shown in FIG. 3. 6 μg of human IgG (as control group), Herceptin, cRC48, and RC48 were respectively incubated with two types of breast cancer cells: SK-BR-3 and BT4745 separately, as well as HER2$^-$ MDA-MB468 cells ($2 \times 10^7$ cells), on ice for 30-45 minutes. After thoroughly washed with 4 mL of cold PBS twice, the antibodies binding to the cell surface were detected by R-PE-conjugated goat anti-human IgG Fc (15 μl, 25 μg/mL) secondary antibody, and then analyzed by flow cytometer (BDFACSCalibur). Human IgG1 in the control group did not show binding to the above three cancer cells. In contrast, Herceptin, cRC48, and RC48 bind strongly to two types of HER2-positive cells, but not to HER2-negative cells, indicating that this binding is HER2-specific (see FIG. 4a). By comparing the average fluorescence intensity in the same group, it was found that RC48 showed higher binding affinity than Herceptin and cRC48. By titrating the concentration of anti-HER2 antibody and the number of cells analyzed in flow cytometry, the binding curve of cell-based anti-HER2 antibody to cell surface HER2 was obtained. The results are shown in FIG. 4b. The humanized anti-HER2 antibody RC48 showed obvious binding affinity to HER2, of which the binding affinity Kd to HER2 on the surface of BT474 cells was 4 nM, while Herceptin and cRC48 were 10 nM and 5 nM, respectively. The results are shown in Table 3:

| Sample | Binding affinity Kd |
|---|---|
| Herceptin | 10 nM |
| cRC48 | 5 nM |
| RC48 | 4 nM |

2) Antigen Binding Specificity Test

Figure 5:
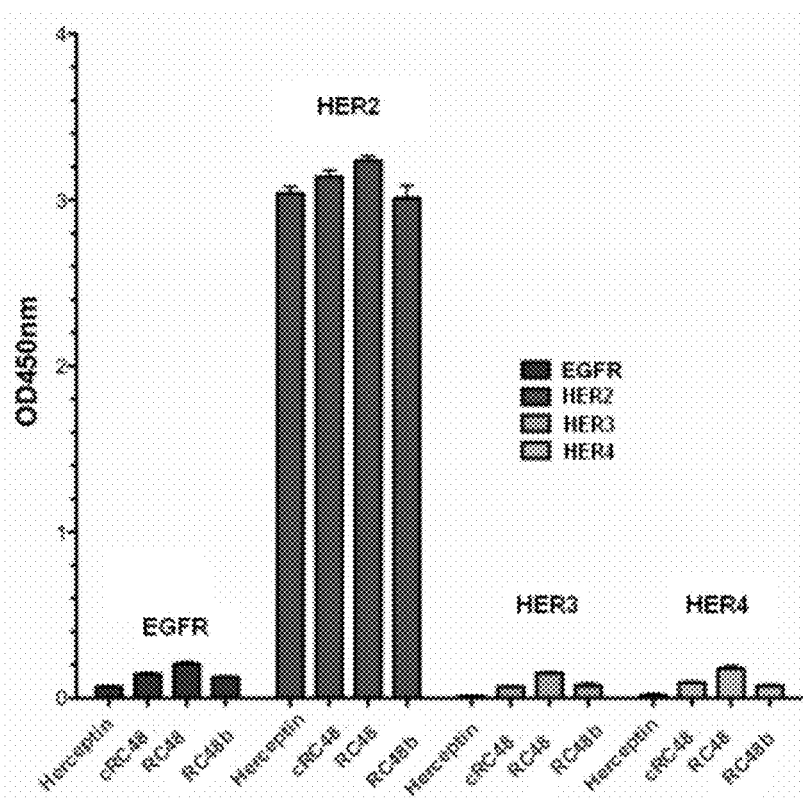
FIG. 5 shows that RC48 only shows specific binding affinity tor HER2, but not to EGFR, HER3, and HER4.

ELISA was used to determine the binding ability of Herceptin, cRC48, RC48 to different surface antigens: EGFR, HER2, HER3, HER4. The ELISA was carried out as described in Example 1. A 96-well plate was coated with EGFR, HER2, HER3 or HER4, 20 ng for each well, incubated with different anti-HER2 antibodies, i.e., Herceptin, cRC48, and RC48, and then detected using HRP-conjugated goat F (ab')$_2$ anti-mouse IgG-Fc secondary antibody (Invitrogen). The results are shown in FIG. 5. It indicates that Herceptin, cRC48, and RC48 have nearly no binding capacity for EGFR, HER3, and HER4, while have strong binding capacity for HER2, demonstrating that Herceptin and RC48 have a high binding specificity for HER2.

Example 5. Preparation of Antibody-Drug Conjugates

1) Purification of Monoclonal Antibody RC48

Monoclonal antibody RC48 was collected from the supernatant of CHO cell culture using Protein A. The antibody was subjected to SDS-PAGE electrophoresis and SEC analysis and the purity was over 95%. The obtained antibody was dialyzed with a PBS buffer in a 30 KD cutoff membrane bag, and concentrated. The antibody concentration was calibrated using a UV absorbance meter for subsequent conjugation.

2) Conjugation of Monoclonal Antibody RC48 with Drug

Reducing agent and protecting agent were respectively prepared with PBS buffer as follows: 1-20 mmol/L TCEP (Tris-2-carboxyethyl-phosphine), 1-20 mmol/L DTPA (Diethylene triamine pentacetate acid) stock solution. The reducing agent was added within a certain concentration range according to the desired coupling ratio, mixed with a certain concentration of monoclonal antibodies (such as: 5-30 mg/mL) according to a certain volume ratio (such as 1:1), so that the final molar ratio of TCEP to antibody is 0.5-6.0:1, and stirred at 25° C. for 2 h. The free thiol group concentration was detected by DTNB method at 412 nm, and the number of free thiol groups was calculated by the molar ratio with the antibody. TCEP reduction has a good reproducibility, and the number of free thiol groups can reach 1.0-8.0 after reduction.

The antibodies can be directly subjected to conjugation after TCEP reduction. A certain concentration (10 mM) of drug (vc-MMAE, vc-MMAF, or mc-MMAF) (purchased from Shanghai HaoYuan Chemical Technology Co., Ltd.) was prepared in 25% DMSO (dimethyl sulfoxide). The drug was added slowly to the antibody solution according to a molar ratio of the drugs to thiol group at 0.3-2.8:1, and stirred to react at 25° C. for 2 h. DTNB method was used to detect the concentration of free thiol group (close to 0) at 412 nm. Remaining unreacted drugs were removed by Sephadex G-25 and free small molecules such as DMSO. SDS-PAGE, R-HPLC and HIC-HPLC were used to detect the conjugation.

Example 6. Binding Affinity of the Antibody Drug Conjugates

Binding Affinity Test by ELISA

The ELISA plate was coated with the recombinant protein HER2-ECD (concentration: 0.5 mg/ml), and incubated overnight at 2° C. to 8° C. After the plate was washed with a plate washer for 3 times, 3% BSA-PBST solution was added for blocking at 37° C. for 2 h, and then the plated was washed with a plate washer for 3 times. Sample loading: the standard, starting from 1000 ng/mL, was diluted with PBST buffer to obtain 11 dilution points, 100 μL/well, incubated at 37° C. for 2 h. The plate was washed with a plate washer for 3 times. The secondary antibody (goat anti-human IgG-Fc-HRP) was diluted 5000-fold with PBST buffer. TMB developing solution was added and incubated at room temperature in the dark for 8-10 minutes. The reaction was terminated by 2M H$_2$SO$_4$, and microplate reader was used for reading at 450/655 nm. The results are shown in Table 4.

TABLE 4

| Comparison of binding affinity of antibody-drug conjugates (VC is short for mc-vc-pAB) and T-DM1 | | |
|---|---|---|
| Sample | Binding affinity ng/mL | Mole equivalent |
| RC48-VC-MMAE | 2.237 | 15.22 |
| RC48-VC-MMAF | 3.349 | 13.51 |
| RC48-MC-MMAF | 2.902 | 16.42 |
| T-DM1 | 2.376 | 15.16 |

As shown in the results, of RC48-VC-MMAE (i.e. RC48-mc-vc-pAB-MMAE), RC48-VC-MMAF, and RC48-MC-MMAF have binding affinity to HER2-ECD equivalent to T-DM1.

Example 7. Efficacy and Safety Test of Monotherapy for HER2-Positive Locally Advanced or Metastatic Urothelial Carcinoma The purpose of this experiment was to evaluate the efficacy and safety of monotherapy for HER2-positive locally advanced or metastatic urothelial carcinoma. The antibody-drug conjugate for test was RC48-mc-vc-pAB-MMAE. RC48 was coupled with MMAE via linker mc-vc-pAB, and the number of coupling drugs varied from 1 to 8.

The selection criteria for the subjects are:

Age: 18 years (minimum age) to 80 years (maximum age) old;

wherein the selection criteria are:

1. The subjects agree to participate in the research and sign an informed consent;
2. Male or female, 18 to 60 years old;
3. Expected survival time is 12 weeks or more;
4. Locally advanced or metastatic bladder urothelial carcinoma which cannot be completely removed by surgery based on pathological diagnosis;
5. Subjects who have been diagnosed as locally advanced or metastatic carcinoma that cannot be removed by surgery, and still have disease progression or resistance after receiving at least a first-line systemic chemotherapy;

6. At least have measurable lesions specified by RECIST 1.1 standard;

7. Positive HER2 expression confirmed by the test laboratory;

8. ECOG physical status is 0 or 1 score;

9. Adequate heart, bone marrow, liver, and kidney functions;

10. Female subjects should be surgically sterilized or postmenopausal patients, or agree to use at least one medically approved contraceptive measures (such as an intrauterine device, contraceptive pills or condoms) during the treatment period and within 6 months after the treatment; male subjects should agree to use at least one medically approved contraceptive measures (such as condoms, abstinence, etc.) during the treatment period and within 6 months after the end of the treatment;

11. Be willing and able to follow trial and follow-up procedures.

Meanwhile, the exclusion criteria are:

1. Known to be allergic to recombinant humanized anti-HER2 monoclonal antibody-MMAE conjugate and components thereof;

2. Received other anti-tumor treatments within 4 weeks before the treatment;

3. Previously received a recombinant humanized anti-HER2 monoclonal antibody-MMAE conjugate;

4. Subjected to major surgery within 4 weeks before the start of administration and not fully recovered;

5. Received with live vaccine within 4 weeks prior to administration or plan to receive any vaccine during treatment period;

6. Having other severe and uncontrollable concomitant diseases that may affect protocol compliance or interfere with interpretation of results;

7. Having other malignant tumors within 5 years before the start of administration;

8. Suffering from CNS metastatic and/or cancerous meningitis;

9. Having active autoimmune disease that requires systemic treatment in the past 2 years;

10. Previously received allogeneic hematopoietic stem cell transplant or solid organ transplant;

11. Having a large amount of pleural fluid or ascites with clinical symptoms or requiring symptomatic treatment;

12. Pregnant or lactating women;

13. Positive HIV test results;

14. Patients with active hepatitis B or C;

15. History of active tuberculosis;

16. Suffering from any other diseases, abnormal metabolism, abnormal results of physical examination or abnormal laboratory test, according to the researcher's judgment, it is reasonable to suspect that the subject has a certain disease or condition unsuitable for using the research drug, or affect the interpretation of the research results, or put the patient at high risk;

17. Who is estimated to have enough patient compliance to this clinical study.

Experimental Methods

This study include subjects with locally advanced or metastatic urothelial carcinoma who had previously failed or resistant to at least first-line systemic chemotherapy, and had measurable lesions, acceptable physical conditions and organ functions. The tumor tissue pathological sections of the subjects were submitted to the laboratory for HER2 expression confirmation, and the positive result was defined by score 2+ or 3+ in immunohistochemistry (IHC) assay (regardless the results of fluorescence in situ hybridization [FISH] detection).

The results determination of HER2 in immunohistochemistry (IHC) was according to the criteria for HER2 interpretation in "Guideline for HER2 detection in breast cancer (2014 Edition, China)". The details are shown in Table 5.

TABLE 5

Criteria for HER2 interpretation in "Guideline for HER2 detection in breast cancer (2014 Edition, China)".

| Scoring criteria | IHC results | Up-regulated HER2 expression level |
|---|---|---|
| No cell membrane staining or ≤10% of invasive cancer cells showed incomplete, weak cell membrane staining. | 0 | negative |
| >10% of invasive cancer cells showed weak and incomplete cell membrane staining. | 1+ | negative |
| >10% of invasive cancer cells showed incomplete and/or weak to moderate cell membrane staining or ≤10% of invasive cancer cells showed strong and intact cell membrane staining. | 2+ | positive |
| >10% of invasive cancer cells showed strong, complete, and uniform cell membrane staining. | 3+ | positive |

Subjects meeting all the criteria received RC48-ADC treatment (2.0 mg/kg, intravenous infusion, once every 2 weeks), and the efficacy was evaluated every 6 weeks until disease progressed, intolerable toxicity was produced or the subject dropped out. The primary endpoint of the study was the objectively assessed objective response rate (ORR). The secondary endpoints were progression-free survival, overall survival, and safety of treatment.

Research Results

The study was launched in December 2017. As of Jul. 31, 2018, a total of 18 subjects received treatment, including 15 males and 3 females, with a median age of 63 years. The primary lesions included the bladder (50.0%), renal pelvis (27.8%), and ureter (22.2%). The main metastatic sites were lung, liver, and lymph node. 16 patients (88.9%) had previously received first-line platinum therapy. The immunohistochemical (IHC) results for HER2 expression (performed by the laboratory) showed that there were 11 (61.1%) IHC2+ subjects and 7 (38.9%) IHC3+ subjects.

Efficacy evaluation was performed on 13 of the 18 subjects, and 10 subjects had partial remission (PR) (wherein 4 subjects had confirmed PR (two consecutive PRs are called confirmed PRs)). According to the RECIST standard: "when every subject meets the criteria for partial or complete remission and the efficacy is confirmed again at a later time point (usually four weeks later), then the complete or partial remission can be established". That is, two consecutive evaluations of PR for a subject is called confirmed PR. The other 6 cases have not yet reached the time point for confirming the efficacy, and only one confirmation has been completed. The objective response rate (ORR) is 76.9% (10/13), and the disease control rate (DCR) (10 cases out of 13 subjected to efficacy evaluation were PRs and 2 cases were stable disease (SD)) were 92.3% (12/13). The current maximum treatment period received by the subjects was more than 7 months. Among the subjects achieved remission, 7 (53.8%) had received taxane treatment and 4 (30.8%) had received PD-1/PD-L1 treatment.

16 of the 18 subjects were subject to safety evaluation. The most common treatment-related adverse reactions (TRAE5) in safety evaluation were elevated ALT (50.0%, grade 1-2), hypoesthesia (50.0%, grade 1-2) and reduced white blood cell count (50.0%, grade 1-2); TRAE which is greater than grade 3 is a decrease in neutrophil count (12.5%, grade 3). No drug-related serious adverse events (SAE) occurred.

Figure 6:
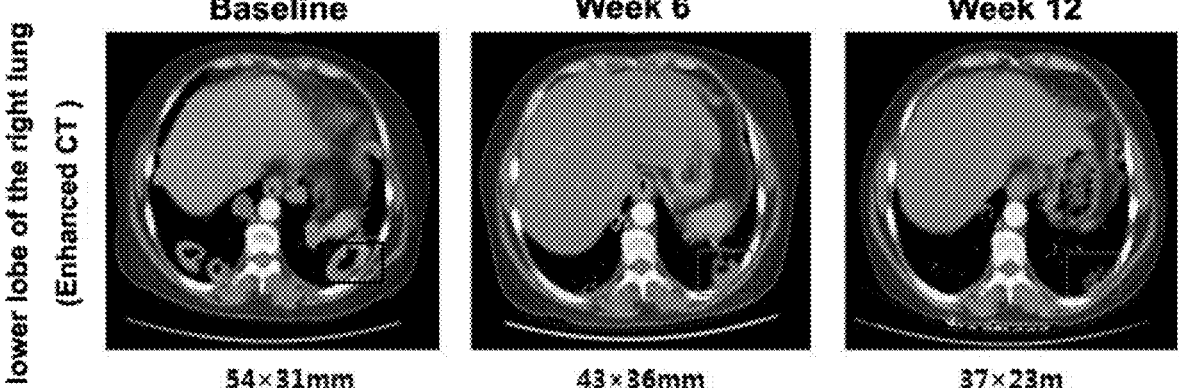
FIG. 6 is the schematic diagram of the efficacy of subject No. 01001. Patient profile: female, 57 years old, with multiple lung metastases after right pelvic cancer surgery. Pathological diagnosis of urothelial carcinoma, HER2 IHC 3+.

Descriptions of the obvious effects of the treatment in some cases are shown as follows:

1. Patient 01001: Female, 57 years old, with multiple lung metastases after right pelvic cancer surgery. Pathological diagnosis of urothelial carcinoma, HER2 IHC 3+;

According to FIG. 6, after 12 weeks of treatment, the tumor lesions in the lower lobe of the right lung were reduced from 54×31 mm (6 weeks of treatment) to 37×23 mm (12 weeks of treatment), decreased by 49%.

Figure 7:
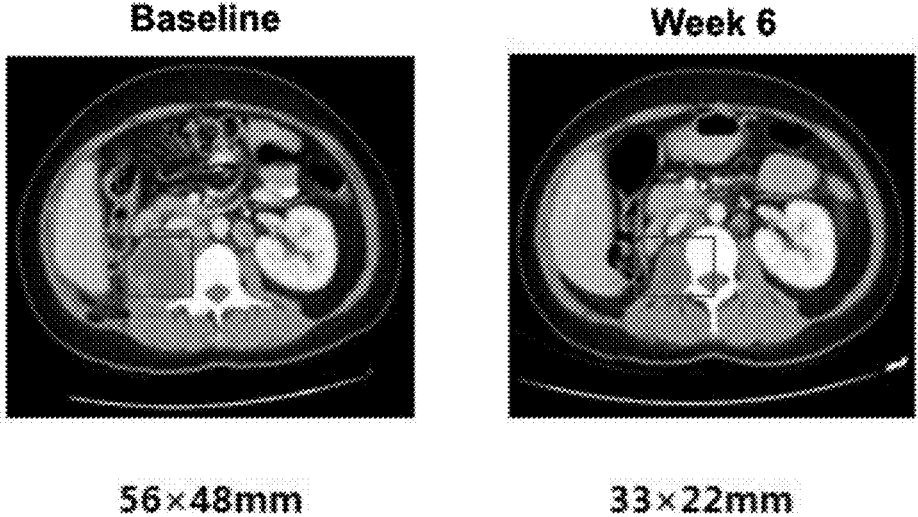
FIG. 7 is the schematic diagram of the efficacy of subject No. 01003. Patient profile: female, 45 years old, abdominal lymph node metastasis after right renal pelvis cancer surgery. Pathological diagnosis of urothelial carcinoma, HER2 IHC 3+.

2. Patient 01003: Female, 45 years old, with abdominal lymph node metastasis after right pelvic cancer surgery. Pathological diagnosis of urothelial carcinoma, HER2 IHC 3+;

According to FIG. 7, after 6 weeks of treatment, the tumor lesion located beside the right psoas major muscle has been reduced from 56×48 mm to 33×22 mm, decreased by 72.9%.

Figure 8:
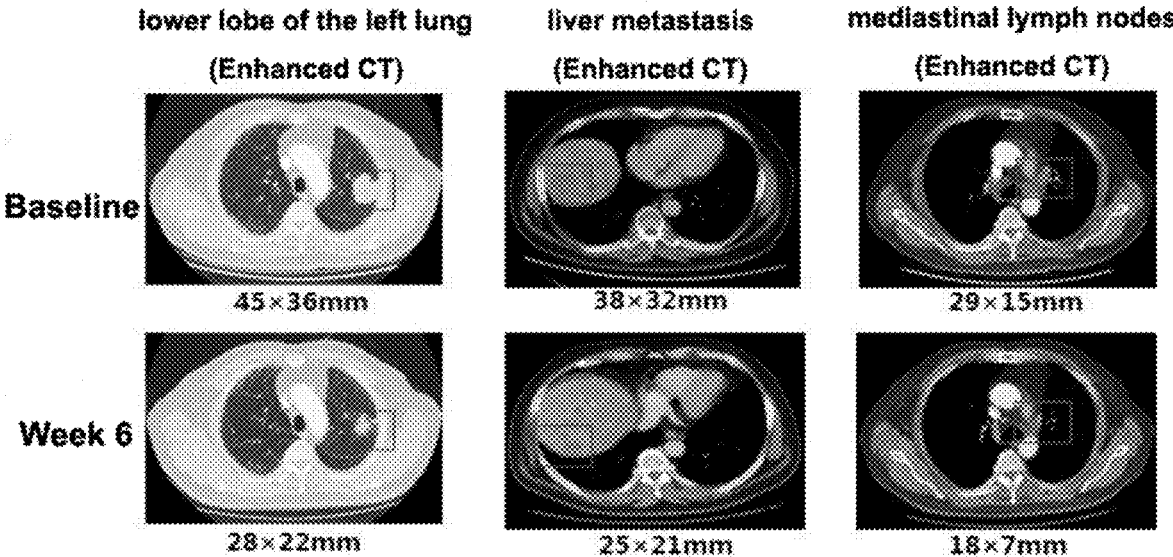
FIG. 8 is the schematic diagram of the efficacy of subject No. 01007. Patient profile: Male, 63 years old, after bladder cancer and right pelvic cancer surgery, lung metastasis, liver metastasis, cervical lymph node metastasis, mediastinal metastasis, multiple bone metastases. Pathological diagnosis of urothelial carcinoma, HER2 IHC 3+.

3. Patient 01007: Male, 63 years old, with lung metastasis, liver metastasis, cervical lymph node metastasis, mediastinal metastasis and multiple bone metastasis after bladder cancer, and right pelvic cancer surgery. Pathological diagnosis of urothelial carcinoma, HER2 IHC 3+;

According to FIG. 8, it can be seen that after 6 weeks of treatment, the tumor lesions located in the left upper lobe, liver metastasis and mediastinal lymph nodes were significantly reduced. The tumor located in the left upper lobe was reduced from 45×36 mm to 28×22 mm, decreased by 61.9%; the tumor in the liver metastasis site was reduced from 38×32 mm to 25×21 mm, decreased by 56.8%; and the tumor in the mediastinal lymph nodes was reduced from 29×15 mm to 18×7 mm, decreased by 71.03%.

The above clinical data and visual pathological changes have shown that the anti-HER2 monoclonal antibody-MMAE conjugate of the present disclosure has a very significant therapeutic effect. It can also be seen through comparison with the currently marketed drugs that it is significantly better than the current similar drugs approved by the European Union and the United States. For example, Atezolizumab (Roche) has an ORR of only 23% in Phase III clinical data and Nivolumab (Bristol-Myers Squibb) merely 19.6%. Erdafitinib (Jansen) only targets patients with urothelial cancer with certain FGFR gene mutations. In contrast, the ORR of the recombinant humanized anti-HER2 monoclonal antibody-MMAE conjugate of the present disclosure is 76.9%, and the disease control rate (DCR) is 92.3%, which is significantly better than similar drugs currently on the market, and the side effects are also significantly smaller than similar drug, without any serious adverse effects (SAE). These make it more available to patients, providing another option for patients with urothelial cancer in need of treatment. It can be seen that the anti-HER2 antibody conjugate of the present disclosure has excellent application prospects in the treatment of urothelial carcinoma, can effectively improve, or even reverse the disease development process in patients, and has achieved unexpected technical effects.

The invention claimed is:

1. A method for treating urothelial carcinoma, comprising administering an antibody-drug conjugate (ADC) to a subject in need thereof, wherein the antibody-drug conjugate is an anti-HER2 antibody or a functional fragment thereof coupled to a cytotoxic molecule; wherein the ADC is represented by formula Ab-(L-U)n, wherein Ab is the antibody or the functional fragment thereof, L is a linker, U is a conjugated cytotoxic molecule, and n is an integer from 1 to 8, representing the number of therapeutic agent molecules bound to the antibody; wherein the anti-HER2 antibody or the functional fragment thereof comprises a heavy chain variable region and a light chain variable region, wherein (i) the heavy chain variable region comprises three CDRs, wherein the amino acid sequences of the CDRs are respectively set forth in SEQ ID NO: 1, 2 and 3, and the light chain variable region comprises three CDRs, wherein the amino acid sequences of the CDRs are respectively set forth in SEQ ID NO: 4, 5 and 6; wherein the linker L is a maleimidocaproyl valine citrulline p-amino-benzyl (mc-vc-pAB) linker; and wherein the conjugated cytotoxic molecule U is MMAE; and wherein administration of the ADC to the subject results in a partial remission (PR) or stable disease (SD).

2. The method according to claim 1, wherein the cytotoxic molecule is conjugated to the antibody through site-directed or undirected conjugation.

3. The method according to claim 1, wherein the antibody or the functional fragment thereof is a murine or chimeric antibody or fragment.

4. The method according to claim 1, wherein the antibody or the functional fragment thereof is derived from the antibody secreted by the hybridoma deposited at the China General Microbiological Culture Collection Center of China Committee for Culture Collection of Microorganisms on Aug. 22, 2013, with an accession number of CGMCC No. 8102.

5. The method according to claim 1, wherein the antibody or functional fragment thereof is a humanized antibody or fragment.

6. The method according to claim 5, wherein the antibody is the antibody secreted by CHO cells deposited at the China Center for Type Culture Collection on Nov. 6, 2013, with an accession number of CCTCC C2013170.

7. The method according to claim 1, wherein the urothelial carcinoma is selected from the group consisting of locally developed urothelial carcinoma which cannot be removed by surgery, locally advanced or metastatic urothelial carcinoma, HER2-positive urothelial carcinoma and HER2-positive locally advanced or metastatic urothelial carcinoma.

8. The method according to claim 7, wherein the urothelial carcinoma is locally developed urothelial carcinoma which cannot be removed by surgery.

9. The method according to claim 7, wherein the urothelial carcinoma is locally advanced or metastatic urothelial carcinoma.

10. The method according to claim 7, wherein the urothelial carcinoma is HER2-positive urothelial carcinoma.

11. The method according to claim 7, wherein the urothelial carcinoma is HER2-positive locally advanced or metastatic urothelial carcinoma.

12. The method according to claim 1, wherein the antibody-drug conjugate further comprises a pharmaceutically acceptable carrier.

13. The method according to claim 12, wherein the antibody-drug conjugate is in a form of a lyophilized formulation or a liquid formulation.

14. The method according to claim 12, wherein the pharmaceutically acceptable carrier comprises one or more of: a stabilizer, a protective agent, a buffer, a lyoprotectant, an activity protective agent, a surfactant, an adsorption carrier, and an absorption promoter.

15. The method according to claim 1, wherein the antibody-drug conjugate is administered intranasally, subcutaneously, intradermally, intramuscularly, or intravenously.

16. The method according to claim 1, wherein administration of the ADC to the subject results in a partial remission (PR).

17. The method according to claim 1, wherein administration of the ADC to the subject does not result in a serious adverse event (SAE).

* * * * *

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: VH CDR1

<400> SEQUENCE: 1

Asp Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: VH CDR2

<400> SEQUENCE: 2

Arg Val Asn Pro Asp His Gly Asp Ser Tyr Tyr Asn Gln Lys Phe Lys
1               5                   10                  15

Asp

<210> SEQ ID NO 3
<211> LENGTH: 9
<212> TYPE: PRT
<213> ORGANISM: Artificial Sequence
<220> FEATURE:
```

<223> OTHER INFORMATION: VH CDR3

<400> SEQUENCE: 3

Ala Arg Asn Tyr Leu Phe Asp His Trp
1               5

<210> SEQ ID NO 4
<211> LENGTH: 11
<212> TYPE: PRT
<213> ORGANISM: Artificial Sequence
<220> FEATURE:
<223> OTHER INFORMATION: VL CDR1

<400> SEQUENCE: 4

Lys Ala Ser Gln Asp Val Gly Thr Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: VL CDR2

<400> SEQUENCE: 5

Trp Ala Ser Ile Arg His Thr
1               5

<210> SEQ ID NO 6
<211> LENGTH: 7
<212> TYPE: PRT
<213> ORGANISM: Artificial Sequence
<220> FEATURE:
<223> OTHER INFORMATION: VL CDR3

<400> SEQUENCE: 6

His Gln Phe Ala Thr Tyr Thr
1               5

<210> SEQ ID NO 7
<211> LENGTH: 26
<212> TYPE: DNA
<213> ORGANISM: Artificial Sequence
<220> FEATURE:
<223> OTHER INFORMATION: P1 primer

<400> SEQUENCE: 7
cgggatcctg ccaccagctg tgcgcc                                    26

<210> SEQ ID NO 8
<211> LENGTH: 28
<212> TYPE: DNA
<213> ORGANISM: Artificial Sequence
<220> FEATURE:
<223> OTHER INFORMATION: P2 primer

<400> SEQUENCE: 8
gctctagatc agttgatggg gcaaggct                                  28

<210> SEQ ID NO 9
<211> LENGTH: 22
<212> TYPE: DNA
<213> ORGANISM: Artificial Sequence
<220> FEATURE:
<223> OTHER INFORMATION: mRC48-VL-1 primer

<400> SEQUENCE: 9
gttggtgcag catcagcccg tt                                          22

<210> SEQ ID NO 10
<211> LENGTH: 23
<212> TYPE: DNA
<213> ORGANISM: Artificial Sequence
<220> FEATURE:
<223> OTHER INFORMATION: mRC48-VL-2

<400> SEQUENCE: 10
gttcactgcc atcaatcttc cac                                         23

<210> SEQ ID NO 11
<211> LENGTH: 20
<212> TYPE: DNA
<213> ORGANISM: Artificial Sequence
<220> FEATURE:
<223> OTHER INFORMATION: mRC48-VH-1

<400> SEQUENCE: 11
gccagtggat agacagatgg                                             20

<210> SEQ ID NO 12
<211> LENGTH: 21
<212> TYPE: DNA
<213> ORGANISM: Artificial Sequence
<220> FEATURE:
<223> OTHER INFORMATION: mRC48-VH-2

<400> SEQUENCE: 12
aggtcactgt cactggctca g                                           21

<210> SEQ ID NO 13
<211> LENGTH: 31
<212> TYPE: DNA
<213> ORGANISM: Artificial Sequence
<220> FEATURE:
<223> OTHER INFORMATION: VH1 primer

<400> SEQUENCE: 13
cgcggatccg ccgccaccat gggatggagc t                                31

<210> SEQ ID NO 14
<211> LENGTH: 42
<212> TYPE: DNA
<213> ORGANISM: Artificial Sequence
<220> FEATURE:
<223> OTHER INFORMATION: VH2 primer

<400> SEQUENCE: 14
gatgggccct tggtgctagc ggagctcact gtcaccagtg tt                    42

<210> SEQ ID NO 15
<211> LENGTH: 20
<212> TYPE: DNA
<213> ORGANISM: Artificial Sequence
<220> FEATURE:
<223> OTHER INFORMATION: CH1 primer

<400> SEQUENCE: 15
gctagcacca agggcccatc                                             20

<210> SEQ ID NO 16
<211> LENGTH: 29
<212> TYPE: DNA

-continued

```
<213> ORGANISM: Artificial Sequence
<220> FEATURE:
<223> OTHER INFORMATION: CH2 primer

<400> SEQUENCE: 16
ccggaattct ttaccgggag acagggaga                                        29

<210> SEQ ID NO 17
<211> LENGTH: 32
<212> TYPE: DNA
<213> ORGANISM: Artificial Sequence
<220> FEATURE:
<223> OTHER INFORMATION: VL1 primer

<400> SEQUENCE: 17
cgcggatccg ccgccaccat ggacatgagg gt                                    32

<210> SEQ ID NO 18
<211> LENGTH: 40
<212> TYPE: DNA
<213> ORGANISM: Artificial Sequence
<220> FEATURE:
<223> OTHER INFORMATION: VL2 primer

<400> SEQUENCE: 18
gatggtgcag ccacagtacg ctttatctca acttttgtac                            40

<210> SEQ ID NO 19
<211> LENGTH: 19
<212> TYPE: DNA
<213> ORGANISM: Artificial Sequence
<220> FEATURE:
<223> OTHER INFORMATION: CL1 primer

<400> SEQUENCE: 19
cgtactgtgg ctgcaccat                                                   19

<210> SEQ ID NO 20
<211> LENGTH: 29
<212> TYPE: DNA
<213> ORGANISM: Artificial Sequence
<220> FEATURE:
<223> OTHER INFORMATION: CL2 primer

<400> SEQUENCE: 20
ccggaattca cactctcccc tgttgaagc                                        29
```